US005955274A

United States Patent [19]

Ligon et al.

[11] Patent Number: 5,955,274

[45] **Date of Patent: *Sep. 21, 1999**

[54] DETECTION OF FUNGAL PATHOGENS USING THE POLYMERASE CHAIN REACTION

[75] Inventors: James M. Ligon, Apex; James J. Beck, Cary, both of N.C.

[73] Assignee: Novartis Finance Corporation, New York, N.Y.

[ * ] Notice: This patent is subject to a terminal disclaimer.

[21] Appl. No.: 08/722,187

[22] PCT Filed: Apr. 19, 1995

[86] PCT No.: PCT/US95/04712

§ 371 Date: Oct. 15, 1996

§ 102(e) Date: Oct. 15, 1996

[87] PCT Pub. No.: WO95/29260

PCT Pub. Date: Nov. 2, 1995

Related U.S. Application Data

[63] Continuation-in-part of application No. 08/233,608, Apr. 25, 1994, Pat. No. 5,585,238.

[51] Int. Cl.$^{6}$ .............................. C12Q 1/68; C07H 21/02; C07H 21/04; C12P 19/34

[52] U.S. Cl. ............................ 435/6; 536/23.1; 536/24.3; 435/91.2

[58] Field of Search ..................... 435/91.2, 6; 536/23.1, 536/24.3, 91.1

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 5,324,632 | 6/1994 | Weisburg et al. | 435/6 |
| 5,447,848 | 9/1995 | Barns et al. | 435/29 |
| 5,585,238 | 12/1996 | Ligon et al. | 435/6 |

FOREIGN PATENT DOCUMENTS

| | | |
|---|---|---|
| WO 91/41001 | 9/1991 | WIPO . |

OTHER PUBLICATIONS

Ursi et al., APMIS 100: 635–639 (1992).

The Stratagene Catalog, p. 39 (1988).

Johanson et al. Use of PCR for detection of *Mycosphaerella fijiensis* and *M. Musicola*", the causal agents of Sigatoka leaf spots in banana and plantain", *Mycol. Res.,* 97:670–674 (1993).

Nazar, R.N., et al, "Potential use of PCR–amplified ribosomal intergeneic sequences in the detection and differentiation of verticillium wilt pathogens", *Physiol. and Molec. Plant Pathol.,* 39:1–11 (1991).

Poupard et al., "Molecular characterization of *Pseudocercosporella herpotrichoides* isolates by amplification of ribosomal DNA internal transcribed spaces", *Plant Pathology,* 42: 873–881 (1993).

Schesser et al., "Use of Polymerase Chain Reaction To Detect the Take–All Fungus, *Gaeumannomyces graminis,* in Infected Wheat Plants", *Applied and Environ. Microbiol.,* 57(2):553–556 (1991).

Stratagene Catalog, 1988, p.39.

Tisserat et al., "Selective Amplification of rDNA Internal Transcribed Spacer Regions to Detect *Opiosphaerella korrae* and *O. herpotricha*", *Phytopathology,* 84(5): 478–482 (1994).

White, T.J., et al., "Amplification and Direct Sequencing of Fungal Ribosomal RNA Genes for Phylogenetics", In: *PCR Protocols*; Academic Press Inc., pp. 315–322 (1990).

Xue et al., "Pathotype identification of *Leptosphaeria maculans* with PCR and oligonucleotide primrers from ribosomal internal transribed spacer sequences", *Physiological and Molecular Plant Pathology,* 41: 179–188 (1992).

International Search Report Jul. 20, 1995.

GenBank Accession No. UO4237, computer printout, Jan. 3, 1994.

Gene characterization kits. Stratagene Catalog, 1988.

*Primary Examiner*—W. Gary Jones
*Assistant Examiner*—Ethan Whisenant
*Attorney, Agent, or Firm*—J. Timothy Meigs

[57] ABSTRACT

DNA sequences from the Internal Transcribed Spacers of the ribosomal RNA gene region are described for different species and strains of Septoria, Pseudocercosporella, Fusarium and Mycosphaerella. Specific primers from within these sequences are identified as being useful for the identification of the fungal isolates using PCR-based techniques.

42 Claims, 9 Drawing Sheets

```
                        10        20        30        40        50        60
                         |         |         |         |         |         |
pCRSTRIT1.con  TCCGTAGGTGAACCTGCGGAGGGATCATTA~~~~~~~~~~~~~~~~~~~~~~~~~~~~~~
pCRSNOD31.con  TCCGTAGGTGAACCTGCGGAAGGATCATTA~~~~~~~~~~~~~~~~~~~~~~~~~~~~~~
pCRW2-1.con    TCCGTAGGTGAACCTGCGGAAGGATCATTAATAGAGCAATGAACAGACAGCGCCCCGGGA
pCRW5-1.con    TCCGTAGGTGAACCTGCGGAAGGATCATTAATAGAGCAATGAACAGACAGCGCCCTGGGA
pCRR1-21.con   TCCGTAGGTGAACCTGCGGAAGGATCATTAATAGAGCAATGGATAGACAGCGCCCCGGGA
Mfij.con       TCCGTAGGTGAACCTGCGGAGGGATCATTA~~~~~~~~~~~~~~~~~~~~~~~~~~~~~~
Mmus.con       TCCGTAGGTGAACCTGCGGGGGGATCATTA~~~~~~~~~~~~~~~~~~~~~~~~~~~~~~

                        70        80        90       100       110       120
                         |         |         |         |         |         |
pCRSTRIT1.con  ~~~~C~~~~~~~~~~~~~~~~~CG~AGCGAGG~~~~~GCCTCCGGGTCCG~~~~~~~~~~
pCRSNOD31.con  ~~~~CACTCAGTAGTTTACTACTG~TAAAAGG~~~~~GGCTGTTAGTCTGTATAGCGCAA
pCRW2-1.con    GAAATCCTGGGGGCTACCCTACTT~GGTAGGGTTTAGAGTCGTCAGGCCGCTCGGAGAAG
pCRW5-1.con    GAAATCCTGGGGGCTACCCTACTTCGGTAGGGTTTAGAGTCGTCAGGCCTCTCGGAGAAG
pCRR1-21.con   GAAATCCTGGGGGCCACCCTACTTCGGTAAGGTTTAGAGTCGTCGGGCCTCTCGGAGAAG
Mfij.con       ~~~~C~~~~~~~~~~~~~~~~~CG~AGTGAGG~~~~~GCTCACG~~CCCG~~~~~~~~~~
Mmus.con       ~~~~C~~~~~~~~~~~~~~~~~CG~AGTGAGG~~~~~GCTCACC~~CCCG~~~~~~~~~~

                       130       140       150       160       170       180
                         |         |         |         |         |         |
pCRSTRIT1.con  ~~~~~~~~~~ACCTCCAACCCTTTGTGAACACAT~CCCGTTGCTTCGG~GGGCGACCCTG
pCRSNOD31.con  GCTGAT~~~GAGCAGCTGGCCTCTTTTATCCACC~CTTGTCTTTTGCG~TACCCACGTTT
pCRW2-1.con    CCTGGTTCAGACCTCCACCCTTGAATAAATTACC~TTTGTTGCTTTGGCAGGGCGCCTCG
pCRW5-1.con    CCTGGTTCAGACCTCCACCCTTGAATAAATTACC~TTTGTTGCTTTGGCAGGGCGCCTCG
pCRR1-21.con   CCTGGTCCAGACCTCCACCCTTGAATAAATTACC~TTTGTTGCTTTGGCAGGGCGCCTCG
Mfij.con       ~~~~~~~~~~ACCTCCAACCCTTTGTGAACCACAACTTGTTGCTTCGG~GGGCGACCTGC
Mmus.con       ~~~~~~~~~~ACCTCCAACCCTTTGTGAACCACA~CCTGTTGCTTCGG~GGGCGACCCTG
```

FIGURE 1A

```
                    190       200       210       220       230       240
                      |         |         |         |         |         |
pCRSTRIT1.con  C~~~~~~~~~~~~~~~CGGGCGCCCCCGGAG~~~GACCACCAAA~~~~~AAAC~~~ACTG
pCRSNOD31.con  C~~~~~~~~~~CTCGGCAGGCTTGCCTGCCG~~~GTTGGACAAATTTATAACC~~~TTTT
pCRW2-1.con    C~~~~~~~~~~GCCAGCGGCTTCGGCTGTTGAGTACCTGCCAGA~~~~~GGACCACAACT
pCRW5-1.con    C~~~~~~~~~~GCCAGCGGCTTCGGCTGTTGAGTACCTGCCAGA~~~~~GGACCACAACT
pCRR1-21.con   C~~~~~~~~~~GCCAGCGGCTTCGGCTGTTGAGTACCTGCCAGA~~~~~GGACCACAACT
Mfij.con       C~~~~~~~~~~GTCGGCGGGCGCCCCCGGAG~~~GCCGTCT~~~~~~~~AAAC~~~ACTG
Mmus.con       CCGGCGAACTTGTCGCCGGGCGCCCCCGGAG~~~GTCTCCT~~~~~~~~TAAC~~~ACTG

                    250       260       270       280       290       300
                      |         |         |         |         |         |
pCRSTRIT1.con  CATCTCTGCGTCGGAGTTT~~ACGA~~GTAAATCGAAACAAAACTTTCAACAACGGATCT
pCRSNOD31.con  TAATTTTCAATCAGCGTCTGAA~AA~~ACTTAATAAT~TACAACTTTCAACAACGGATCT
pCRW2-1.con    CTTGTTTTTAGTGATGTCTGAG~TACTATATAATAGT~TAAAACTTTCAACAACGGATCT
pCRW5-1.con    CTTGTTTTTAGTGATGTCTGAG~TACTATATAATAGT~TAAAACTTTCAACAACGGATCT
pCRR1-21.con   CTTGTTTTTAGTGATGTCTGAG~TACTATATAATAGT~TAAAACTTTCAACAACGGATCT
Mfij.con       CATCTTTGCGTCGGAGTTT~~A~AA~~ACAAATCGAA~CAAAACTTTCAACAACGGATCT
Mmus.con       CATCTCTGCGTCGGAGTTC~~C~AA~~ACAAATCGGA~CAAAACTTTCAACAACGGATCT

                    310       320       330       340       350       360
                      |         |         |         |         |         |
pCRSTRIT1.con  CTTGGTTCTGGCATCGATGAAGAACGCAGCGAAATGCGATAAGTAATGTGAATTGCAGAA
pCRSNOD31.con  CTTGGTTCTGGCATCGATGAAGAACGCAGCGAAATGCGATAAGTAGTGTGAATTGCAGAA
pCRW2-1.con    CTTGGTTCTGGCATCGATGAAGAACGCAGCGAAATGCGATAAGTAATGTGAATTGCAGAA
pCRW5-1.con    CTTGGTTCTGGCATCGATGAAGAACGCAGCGAAATGCGATAAGTAATGTGAATTGCAGAA
pCRR1-21.con   CTTGGTTCTGGCATCGATGAAGAACGCAGCGAAATGCGATAAGTAATGTGAATTGCAGAA
Mfij.con       CTTGGTTCTGGCATCGATGAAGAACGCAGCGAAATGCGATAAGTAATGTGAATTGCAGAA
Mmus.con       CTTGGTTCTGGCATCGATGAAGAACGCAGCGAAATGCGATAAGTAATGTGAATTGCAGAA
```

FIGURE 1B

```
                370       380       390       400       410       420
                  |         |         |         |         |         |
pCRSTRIT1.con  TTCAGTGAATCATCGAATCTTTGAACGCACATTGCGCCCCCTGGTATTCCGGGGGGCATG
pCRSNOD31.con  TTCAGTGAATCATCGAATCTTTGAACGCACATTGCGCCCCTTGGTATTCCATGGGGCATG
pCRW2-1.con    TTCAGTGAATCATCGAATCTTTGAACGCACATTGCGCCCTCTGGTATTCCGGGGGGCATG
pCRW5-1.con    TTCAGTGAATCATCGAATCTTTGAACGCACATTGCGCCCTCTGGTATTCCGGGGGGCATG
pCRR1-21.con   TTCAGTGAATCATCGAATCTTTGAACGCACATTGCGCCCTCTGGTATTCCGGGGGGCATG
Mfij.con       TTCAGTGAATCATCGAATCTTTGAACGCACATTGCGCCCTTTGGTATTCCGAAGGGCATG
Mmus.con       TTCAGTGAATCATCGAATCTTTGAACGCACATTGCGCCCTTTGGCATTCCGAAGGGCATG

                430       440       450       460       470       480
                  |         |         |         |         |         |
pCRSTRIT1.con  CCCGTTCGAGCGTCATT~ACACCACTCCAGCCTC~GCTGGGTATTGGGCGTCTTTTCGCG
pCRSNOD31.con  CCTGTTCGAGCGTCATT~TGTACCCTCAAGCTCT~GCTTGGTGTTGGGTGTT~~~~~~~~
pCRW2-1.con    CCTGTTCGAGCGTCATTATAACCACTCAAGCTCTCGCTTGGTATTGGG~~GT~~~~~~~~
pCRW5-1.con    CCTGTTCGAGCGTCATTATAACCACTCAAGCTCTCGCTTGGTATTGGG~~GT~~~~~~~~
pCRR1-21.con   CCTGTTCGAGCGTCATTATAACCACTCAAGCTCTCGCTTGGTATTGGG~~GT~~~~~~~~
Mfij.con       CCTGTTCGAGCGTCATT~TCACCACTCAAGCCTG~GCTTGGTATTGGGCGTC~~~~~~~~
Mmus.con       CCTGTTCGAGCGTCATT~TCACCACTCAAGCCTA~GCTTGGTATTGGGCGCC~~~~~~~~

                490       500       510       520       530       540
                  |         |         |         |         |         |
pCRSTRIT1.con  GGGGATCACTCCCCCGCGCGCCTCAAAGTCTCC~~~~~~~GGCTGAGCGGTCTCGTCTCC
pCRSNOD31.con  ~~~~~TGTCCTCTCCCTAGTGTTTGGACTCGCCTTAAAA~TAATTGGCAGCC~AGTGTTT
pCRW2-1.con    ~~~~~TCGCGTCCTCGCGGCCTCTAAAATCAGT~~~~~~~GGCGGTGCCTGT~CGGCTCT
pCRW5-1.con    ~~~~~TCGCGTCCTCGCGGCCTCTAAAATCAGT~~~~~~~GGCGGTGCCTCT~CGGCTCT
pCRR1-21.con   ~~~~~TCGCGTCTTCGCGGCCTCTAAAATCAGT~~~~~~~GGCGGTGCCTGT~CGGCTCT
Mfij.con       ~~~~~GCGGTTCTTCGCGCGCCTTAAAGTCTCC~~~~~~~GGCTGAGCTGTC~CGTCTCT
Mmus.con       ~~~~~GCGGTGCTCCGCGCGCCCCAAAGTCTCC~~~~~~CGGCTAAGCCGTC~CGTCTCT
```

FIGURE 1C

```
                         550       560       570       580       590       600
                           |         |         |         |         |         |
pCRSTRIT1.con  CAGCGTTGTGG~~CATCACGTCTCGCCGCGGAGTTCACGAGCCCTCAC~~~~GGCCGTTA
pCRSNOD31.con  TGGTATTGAAGCGCAGCACAAGTCGCGATTCGTA~~ACAAACACTTGC~~~~GTCCACAA
pCRW2-1.con    ACGCGTAGTAATACTCCTCGCGATTGAGTCCGGT~~AGGTTTACTTGCCAGTAACCCCCA
pCRW5-1.con    ACGCGTAGTAATACTCCTCGCGATTGAGTCCGGT~~AGGTTTACTTGCCAGTAACCCCCA
pCRR1-21.con   ACGCGTAGTAATACTCCTCGCGATTGAGTCCGGT~~AGGTTTACTTGCCAGCAACCCCCA
Mfij.con       AAGCGTTGTGG~ATCTTTCAATTCGCTTCGGAGT~~GCGGGTGGCCGC~~~~GGCCGTTA
Mmus.con       AAGCGTTGTGG~ATTTTTCAGTTCGCTCCGGAGC~~GCGGGTGGCCGC~~~~GGCCGTTA

                         610       620       630       640       650       660
                           |         |         |         |         |         |
pCRSTRIT1.con  AATCACA~~~~CCTCAGGTTGACCTCGGATCGGGTAGGGATACCCGCTGAACTTAAGCAT
pCRSNOD31.con  GCCT~~T~~~TTTAACTTTTGACCTCGGATCAGGTAGGGATACCCGCTGAACTTAAGCAT
pCRW2-1.con    ATTT~~T~~~~TTACAGGTTGACCTCGGATCAGGTAGGGATACCCGCTGAACTTAAGCAT
pCRW5-1.con    ATTT~~T~~~~TTACAGGTTGACCTCGGATCAGGTAGGGATACCCGCTGAACTTAAGCAT
pCRR1-21.con   ATTT~~T~~~~TTACAGGTTGACCTCGGATCAGGTAGGGATACCCGCTGAACTTAAGCAT
Mfij.con       AATC~~TTTATTCAAAGGTTGACCTCGGATCAGGTAGGGATACCCGCTGAACTTAAGCAT
Mmus.con       AATC~~T~~~~TCAAAGGTTGACCTCGGATCAGGTAGGGATACCCGCTGAACTTAAGCAT

                         670
                           |
pCRSTRIT1.con  ATCAATAAGCGGAGGA
pCRSNOD31.con  ATCAATAAGCGGAGGA
pCRW2-1.con    ATCAATAAGCGGAGGA
pCRW5-1.con    ATCAATAAGCGGAGGA
pCRR1-21.con   ATCAATAAGCGGAGGA
Mfij.con       ATCAATAAGCGGAGGA
Mmus.con       ATCAATAAGCGGAGGA
```

FIGURE 1D

```
                           10        20        30        40        50        60
                            |         |         |         |         |         |
pCRSNOD31.con  TCC~GTAGGTGAACCTGCGGAAGGATCATTACACTCAGTAGTTTACTACTGTAAAAGGGG
SATITS.CON     TCCCGTAGGTGAACCTGCGGAAGGATCATTACACTCAGTAGTTTACTACTGTAAAGGAGG

                           70        80        90       100       110       120
                            |         |         |         |         |         |
pCRSNOD31.con  CTGTTAGTCTGTATAGCGCAAGCTGATGAGCAGCTGGCCTCTTTTATCCACCCTTGTCTT
SATITS.CON     CTGTTAGTCTGTATAGCGCAAGCTGATGAGCAGCTAGCCTCTTTTATCCACCCTTGTCTT

                          130       140       150       160       170       180
                            |         |         |         |         |         |
pCRSNOD31.con  TTGCGTACCCACGTTTCCTCGGCAGGCTTGCCTGCCGGTTGGACAAATTTATAACCTTTT
SATITS.CON     TTGCGTACCCACGTTTCCTCGGCAGGCTTGCCTGCCGATTGGACAAACCTATAACCTTTT

                          190       200       210       220       230       240
                            |         |         |         |         |         |
pCRSNOD31.con  TAATTTTCAATCAGCGTCTGAAAAACTTAATAATTACAACTTTCAACAACGGATCTCTTG
SATITS.CON     TAATTTTCAATCAGCGTCTGAAAAACTTAATAATTACAACTTTCAACAACGGATCTCTTG

                          250       260       270       280       290       300
                            |         |         |         |         |         |
pCRSNOD31.con  GTTCTGGCATCGATGAAGAACGCAGCGA~AATGCGATAAGTAGTGTGAATTGCAGAATTC
SATITS.CON     GTTCTGGCATCGATGAAGAACGCAGCGACAATGCGATAAGTAGTGTGAATTGCAGAATTC
```

FIGURE 2A

```
                   310        320        330        340        350        360
                     |          |          |          |          |          |
pCRSNOD31.con  AGTGAATCATCGAATCTTTGAACGCACATTGCGCCCCTTGGTATTCCATGGGGCATGCCT
SATITS.CON     AGTGAATCATCGAATCTTTGAACGCACATTGCGCCCCTTGGTATTCCATGGGGCATGCCT

                   370        380        390        400        410        420
                     |          |          |          |          |          |
pCRSNOD31.con  GTTCGAGCGTCATTTGTACCCTCAAGCTCTGCTTGGTGTTGGGTGTTTGTCCTCTCCCTA
SATITS.CON     GTTCGAGCGTCATTTGTACCCTCAAGCTCTGCTTGGTGTTGGGTGTTTGTCCTCTCCCTA

                   430        440        450        460        470        480
                     |          |          |          |          |          |
pCRSNOD31.con  GTGTTTGGACTCGCCTTAAAATAATTGGCAGCCAGTGTTTTGGTATTGAAGCGCAGCACA
SATITS.CON     GTGTTTGGACTCGCCTTAAAATAATTGGCAGCCAGTGTTTTGGTAYTGAAGCGCAGCACA

                   490        500        510        520        530        540
                     |          |          |          |          |          |
pCRSNOD31.con  AGTCGCGATTCGTAACAAACACTTGCGTCCACAAGCC~~TTTTTAACTTTTGACCTCGGA
SATITS.CON     AGTCGCGATTCTTATCAAATACTTGCGTCCACAAGCCCTTTTTTAACTTTTGACCTCGGA

                   550        560        570        580
                     |          |          |          |
pCRSNOD31.con  TCAGGTAGGGATACCCGCTGAACTTAAGCATATCAATAAGCGGAGGA
SATITS.CON     TCAGGTAGGAG~ACC~GCTGA~CTTAA
```

FIGURE 2B

```
                          10        20        30        40        50        60
                           |         |         |         |         |         |
Fculm.con     ~~~~~~~~~~~~~~~~~~GAGGGATCATTACCGAGTTTACTRACTCCCAAACCCCTGTGA
Fgram.con     ~~~~~~~~~~~~~~~~~~~~~GGATCATTACCGAGTTTACWSACTCCCAAACCCCTGTGA
Fpoae.con     TCCGTAGGTGAACCTGCGGAGGGATCATTACCGAGTTTAC~AACTCCCAAACCCCTGTGA
Mniv.con      TCCGTAGGTGAACCTGCGGAGGGATCATTACTGAGTTT~TTAACTCTCCAAACCATGTGA
PCRFmon1.con  TCCGTAGGTGAACCTGCGGAGGGATCATTACCGAGTTTAC~AACTCCCAAACCCCTGTGA

                          70        80        90       100       110       120
                           |         |         |         |         |         |
Fculm.con     ACDTACCTT~ATGTTGCCTCGGCGGATCAGCCCGCGCCCCGTAAAAAGGGACGGCCCGCC
Fgram.con     ACATACCTT~ATGTTGCCTCGGCGGATCAGCCCGCGCCCCG~~~AAAGGGACGGCCCGCC
Fpoae.con     ACATACCWTTATGTTGCCTCGGCGGATCAGCCCGCKCCYYGTAAAACGGGACGGCCCGCC
Mniv.con      ACTTACCAC~~TGTTGCCTCGGTGGAT~GGTGC~TGTCTCTCGGGACGGTRCCACC~GCC
PCRFmon1.con  ACATACCTT~ATGTTGCCTCGGCGGATCAGCCCGCGCCCCGTAAAAAGGGACGGCCCGCC

                         130       140       150       160       170       180
                           |         |         |         |         |         |
Fculm.con     GCAGGAA~CCCTAAACTCTG~~~~TTTTTAGTGGAACTTCTGAGTATAAAAAACAAATAA
Fgram.con     GCAGGAA~CCCTAAACTCTG~~~~TTTTTAGTGGAACTTCTGAGTATAAAAAACAAATAA
Fpoae.con     GCAGGAAACCCTAAACTCTG~~~~TTTTTAGTGGAACTTCTGAGTATAAAAAACAAATAA
Mniv.con      GGTGGACTACCTAAACTCTGTTAATTTTTGYCAA~~~~TCTGAATCAAACTAAGAAATAA
PCRFmon1.con  GCAGGAA~CCCTAAACTCTG~~~~TTTTTAGTGGAACTTCTGAGTATAAAAAACAAATAA

                         190       200       210       220       230       240
                           |         |         |         |         |         |
Fculm.con     ATCAAAACTTTCAACAACGGATCTCTTGGTTCTGGCATCGATGAAGAACGCAGCAAAATG
Fgram.con     ATCAAAACTTTCAACAACGGATCTCTTGGTKCTGGCATCGATGAAGAACGCASCRAAATG
Fpoae.con     ATCAAAACTTTCAACAACGGATCTCTTGGTTCTGGCATCGATGAAGAACGCAGCAAAATG
Mniv.con      GTTAAAACTTTCAACAACGGATCTCTTGGTTCTGGCATCGATGAAGAACGCAGCGAAATG
PCRFmon1.con  ATCAAAACTTTCAACAACGGATCTCTTGGTTCTGGCATCGATGAAGAACGCAGCAAAATG
```

FIGURE 3A

```
                      250       260       270       280       290       300
                        |         |         |         |         |         |
Fculm.con     CGATAAGTAATGTGAATTGCAGAATTCAGTGAATCATCGAATCTTTGAACGCACATTGCG
Fgram.con     CGATAAGTAATGTGWATTGCAGAATTCAGTGAATCAWCGAATCTTTGAACGCWSATTGCK
Fpoae.con     CGATAAGTAATGTGAATTGCAGAATTCAGTGAATCATCGAATCTTTGAACGCACATTGCG
Mniv.con      CGATAAGTAATGTGAATTGCAGAATTCAGTGAATCATCGAATCTTTGAACGCACATTGCG
PCRFmon1.con  CGATAAGTAATGTGAATTGCAGAATTCAGTGAATCATCGAATCTTTGAACGCACATTGCG

                      310       320       330       340       350       360
                        |         |         |         |         |         |
Fculm.con     CCCGCCAGTATTCTGGCGGGCATGCCTGTTCGAGCGTCATTTCAACCCTCAAGCCC~~~A
Fgram.con     MCCRCCAGTATTCTGGCGGGCATGCCTGTTCGAGCGTCATTTCAACCCTCAAGCCC~~~A
Fpoae.con     CCCGCCAGTATTCTGGCGGGCATGCCTGTTCGAGCGTCATTTCAACCCTCAAGCCC~~~A
Mniv.con      CCCATTAGTATTCTAGTGGGCATGCCTGTTCGAGCGTCATTTCAACCCTTAAGCCT~~~A
PCRFmon1.con  CCCGCCAGTATTCTGGCGGGCATGCCTGTTCGAGCGTCATTTCAACCCTCAAGCCC~~~A

                      370       380       390       400       410       420
                        |         |         |         |         |         |
Fculm.con     GCTTGGTGTTGGG~A~~~~~GC~~~~TGCAGTCCTGCTG~~~CACTCCCCAAATACATTG
Fgram.con     GVTTGGTGTKGGGGA~~~~~RY~~~~TGCAGKCCTRYTK~~~CACTCCCCAAATAARTTG
Fpoae.con     GCTTGGTGTTGGG~A~~~~~TC~~~~TTGYGTKMAWWCR~~~CAKTCCCCAAATTGATTG
Mniv.con      GCTTAGTGTTGGGAGACTGCCTAATACGCAGCTCCTCAAAACCAGTGGCGGAGTCGGTTC
PCRFmon1.con  GCTTGGTGTTGGG~A~~~~~GC~~~~TGCAGTCCTGCTG~~~CACTCCCCAAATACATTG

                      430       440       450       460       470       480
                        |         |         |         |         |         |
Fculm.con     GCGGTCACGTCGRAGCT~TCCATAGCGTAGTAATTTACATATCGTTACTGGTAATCGTCG
Fgram.con     GCGGTCACGTCGAA~CT~TCCATAGCGTAGTAAGTTACACATCGTTACTGGTAATCGTCG
Fpoae.con     GCGGTCACGTCGA~GCT~TCCATAGCGTAGTAATTTACACATCGTTACTGGTAATCGTCG
Mniv.con      GTGCTCTGAGCGTAGTAATTTTTTATCTCGCT~TCTGCAAGYCG~GACTGGCAACAGCCA
PCRFmon1.con  GCGGTCACGTCGA~GCT~TCCATAGCGTAGTAATTTACACATCGTTACTGGTAATCGTCG
```

FIGURE 3B

```
                 490       500       510       520       530       540
                   |         |         |         |         |         |
Fculm.con      CGG~CYACGCCGTTAAACCCCAACTTCTGAATGTTGACCTCGGATCAGGTAGGAATACCC
Fgram.con      CGG~CTACGCCGTTAAACCCCAACTTCTGAATGTTGACCTCGGATCAGGTAGGAATACCC
Fpoae.con      CGG~CCACGCCGTTAAACCCCAACTTCTGAATGTTGACCTCGGATCAGGTAGGAATACCC
Mniv.con       TAAACCGCACCCTTCGGGGGCACTTTTTAATGGTTGACCTCGGATCAGGTAGGAATACCC
PCRFmon1.con   CGG~CCACGCCGTTAAACCCCAACTTCTGAATGTTGACCTCGGATCAGGTAGGAATACCC

                 550       560       570
                   |         |         |
Fculm.con      GCTGAA
Fgram.con      GCTGAA~~~~GGTA~~~~~~~~~~~~~~~~A
Fpoae.con      GCTGAACTTAAGCATATCAATAAGCGGAGGA
Mniv.con       GCTGAACTTAAGCATATCAATAAGCGGAGGA
PCRFmon1.con   GCTGAACTTAAGCATATCAATAAGCGGAGGA
```

FIGURE 3C

DETECTION OF FUNGAL PATHOGENS USING THE POLYMERASE CHAIN REACTION

This application is a 371 of PCT/US95/04712 filed Apr. 19, 1995 and a CIP of U.S. Ser. No. 08/233,608 filed Apr. 25, 1994 and now U.S. Pat. No. 5,585,238.

FIELD OF THE INVENTION

The present invention relates to the use of species-specific primers in polymerase chain reaction assays for the detection of fungal pathogens. The use of these primers enables the detection of specific isolates of fungal pathogens and the monitoring of disease development in plant populations.

BACKGROUND OF THE INVENTION

Diseases in plants cause considerable crop loss from year to year resulting both in economic deprivation to farmers and additionally in many parts of the world to shortfalls in the nutritional provision for local populations. The widespread use of fungicides has provided considerable security against plant pathogen attack. However, despite $1 billion worth of expenditure on fungicides, worldwide crop losses amounted to approximately 10% of crop value in 1981 (James, 1981; *Seed Sci. & Technol.* 9: 679–685).

The severity of the destructive process of disease depends on the aggressiveness of the pathogen and the response of the host. One aim of most plant breeding programs is to increase the resistance of host plants to disease. Typically, different races of pathogens interact with different varieties of the same crop species differentially, and many sources of host resistance only protect against specific pathogen races. Furthermore, some pathogen races show early signs of disease symptoms, but cause little damage to the crop. Jones and Clifford (1983; Cereal Diseases, John Wiley) report that virulent forms of the pathogen are expected to emerge in the pathogen population in response to the introduction of resistance into host cultivars and that it is therefore necessary to monitor pathogen populations. In addition, there are several documented cases of the evolution of fungal strains which are resistant to particular fungicides. As early as 1981, Fletcher and Wolfe (1981; *Proc.* 1981 *Brit. Crop Prot. Conf.) contended that* 24% of the powdery mildew populations from spring barley, and 53% from winter barley showed considerable variation in response to the fungicide triadimenol and that the distribution of these populations varied between varieties with the most susceptible variety also giving the highest incidence of less susceptible types. Similar variation in the sensitivity of fungi to fungicides has been documented for wheat mildew (also to triadimenol), Botrytis (to benomyl), Pyrenophora (to organomercury), Pseudocercosporella (to MBC-type fungicides) and *Mycosphaerella fijiensis* to triazoles to mention just a few (Jones and Clifford; Cereal Diseases, John Wiley, 1983).

Cereal species are grown world-wide and represent a major fraction of world food production. Although yield loss is caused by many pathogens, the necrotizing pathogens Septoria and Pseudocercosporella are particularly important in the major cereal growing areas of Europe and North America (Jones and Clifford; Cereal Diseases, John Wiley, 1983). In particular, the differential symptomology caused by different isolates and species of these fungi make the accurate predictive determination of potential disease loss difficult. Consequently, the availability of improved diagnostic techniques for the rapid and accurate identification of specific pathogens will be of considerable use to field pathologists.

Four Septoria species parasitize the small grain species. *Septoria tritici* is the causative agent of leaf blotch and is virulent on wheat but also parasitizes triticale and rye. It typically causes leaf necrosis. *Septoria nodorum* is the causative agent of glume blotch and is parasitic on wheat, triticale, rye and barley and although mainly restricted to glumes is also found on leaf blades and sheaths. *Septoria avenae* is parasitic on oats, wheat and triticale and *Septoria passerinii* is restricted to barley. Septoria diseases occur in all wheat growing areas at economically important levels. Different Septoria diseases frequently occur concurrently within fields and on individual plants, where the disease symptoms may be collectively referred to as the "Septoria complex". Typically, the most commonly found species are *S. tritici* and *S. nodorum*. According to Wiese (1977; Compendium of Wheat Diseases, Amer. Phytopath. Soc. pages 42–45), the Septoria complex presently destroys nearly 2% of the world's wheat annually, the yield loss being mainly the result of impaired grain filling. Fungicide treatments can save up to 20% in cases of severe Septoria infection, but it is often difficult to distinguish between the different Septoria species at the onset of infection and this makes the decision whether or not to invest in fungicide use difficult because different cultivars display differing degrees of resistance to the various Septoria species.

The eyespot disease of cereals is caused by the fungus *Pseudocercosporella herpotrichoides* and is restricted to the basal culm of the plant. Wheat, rye, oats and other grasses are susceptible to the eyespot disease which occurs in cool, moist climates and is prevalent in Europe, North and South America, Africa and Australia. Wheat is the most susceptible cereal species, but isolates have been identified which are also virulent on other cereals. The R-strain of the fungus, for example, has also been isolated from rye and grows more slowly on wheat than the W-strain which has been isolated from wheat. Although eyespot may kill tillers or plants outright, it more usually causes lodging and/or results in a reduction in kernel size and number. Yield losses associated with eyespot are of even greater magnitude than those associated with *Septoria tritici* and *Septoria nodorum*. Typical control measures for eyespot include treatment wit h growth regulators to strengthen intemodes, and fungicide treatment. However, the differing susceptibility of cultivars to different strains of the fungus render the predictive efficacy of fungicide treatments difficult.

Sigatoka leaf spot of banana occurs in two forms each of which is caused by a different fungus. The economically important Black Sigatoka is caused by *Mycosphaerella fijiensis*, whereas the less economically significant Yellow Sigatoka is caused by *Mycosphaerella musicola* (Johanson and Jeger, 1993; Mycol. Res. 97: 670–674). Black Sigatoka is the major problem in banana causing severe losses of 30% and more. Due to occurrence of fungicide resistance in *Mycosphaerella fijiensis*, usage of fungicide should best be limited to prevent the further occurrence of resistance. Consequently, the availability of diagnostic tools will provide an important means of identifying the appropriate circumstances in which to utilize fungicides without unnecessarily risking the development of further resistance.

Thus, there is a real need for the development of technology which will allow the identification of specific races of pathogen fungi early in the infection process. By identifying the specific race of a pathogen before disease symptoms become evident in the crop stand, the agriculturist can assess the likely effects of further development of the pathogen in the crop variety in which it has been identified and can choose an appropriate fungicide if such application is deemed necessary.

SUMMARY OF THE INVENTION

The present invention is drawn to methods of identification of different pathotypes of plant pathogenic fungi. The invention provides DNA sequences which show variability between different fungal pathotypes. Such DNA sequences are useful in the method of the invention as they can be used to derive primers for use in polymerase chain reaction (PCR)-based diagnostic assays. These primers generate unique fragments in PCR reactions in which the DNA template is provided by specific fungal pathotypes and can thus be used to identify the presence or absence of specific pathotypes in host plant material before the onset of disease symptoms.

This invention provides the possibility of assessing potential damage in a specific crop variety-pathogen strain relationship and of utilizing judiciously the diverse armory of fungicides which is available. Furthermore, it can be used to provide detailed information on the development and spread of specific pathogen races over extended geographical areas. The invention provides a method of detection which is especially suitable for diseases with a long latent phase such as those caused by *Septoria nodorum* or *Septoria tritici* on wheat and *Mycosphaerella fijiensis* on banana.

Kits useful in the practice of the invention are also provided. The kits find particular use in the identification of Septoria, Pseudocercosporella, Fusarium, and Mycosphaerella pathogens.

DESCRIPTION OF THE FIGURES

FIGS. 1A–1D Alignment of Internal Transcribed Spacer Sequences from *Septoria tritici, Septoria nodorum, Pseudocercosporella herpotrichoides* strain W (two variants), *Pseudocercosporella herpotrichoides* strain R, *Mycosphaerella fijiensis*, and *Mycosphaerella musicola.*

FIGS. 2A–2B Alignment of the Internal Transcribed Spacer Sequences from *Septoria nodorum* and *Septoria avenae* f.sp. *triticea.*

FIGS. 3A–3C Alignment of the Internal Transcribed Spacer Sequences from *Fusarium graminearum, Fusarium culmorum, Fusarium moniliforme* and *Microdochium nivale.*

DETAILED DESCRIPTION OF THE INVENTION

The present invention provides unique DNA sequences which are useful in identifying different pathotypes of plant pathogenic fungi. Particularly the DNA sequences can be used as primers in PCR based analysis for the identification of fungal pathotypes. The DNA sequences of the invention include the Internal Transcribed Spacer (ITS) of the ribosomal RNA gene regions of particular fungal pathogens as well as primers which are derived from these regions which are capable of identifying the particular pathogen. These ITS DNA sequences from different pathotypes within a pathogen species or genus which vary between the different members of the species or genus can be used to identify those specific members.

Biomedical researchers have used PCR-based techniques for some time and with moderate success to detect pathogens in infected animal tissues. Only recently, however, has this technique been applied to detect plant pathogens. The presence of *Gaumannomyces graminis* in infected wheat has been detected using PCR of sequences specific to the pathogen amitochondrial genome (Schlesser et al., 1991; *Applied and Environ. Microbiol.* 57: 553–556) and random amplified polymorphic DNA (i.e. RAPD) markers were able to distinguish numerous races of *Gremmeniella abietina*, the causal agent of scleroderris canker in conifers.

Ribosomal genes are suitable for use as molecular probe targets because of their high copy number. Despite the high conservation between mature rRNA sequences, the non-transcribed and transcribed spacer sequences are usually poorly conserved and are thus suitable as target sequences for the detection of recent evolutionary divergence. Fungal rRNA genes are organized in units each of which encodes three mature subunits of 18S, 5.8S, and 28S respectively. These subunits are separated by two internal transcribed spacers, ITS1 and ITS2, of around 300 bp (White et al., 1990; In: PCR Protocols; Eds.: Innes et al.; pages 315–322). In addition, the transcriptional units are separated by non-transcribed spacer sequences (NTSs). The ITS and NTS sequences are particularly suitable for the detection of specific pathotypes of different fungal pathogens.

The DNA sequences of the invention are from the Internal Transcribed Spacer (ITS) of the ribosomal RNA gene region of different plant pathogens. The ITS DNA sequences from different pathotypes within a pathogen species or genus vary between the different members of the species or genus. Once having determined the ITS sequences of a pathogen, these sequences can be aligned with other ITS sequences. In this manner, primers can be derived from the ITS sequences. That is, primers can be designed based on regions within the ITS regions that contain the greatest differences in sequence among the fungal pathotypes. These sequences and primers based on these sequences can be used to identify specific pathogen members.

Particular DNA sequences of interest include ITS DNA sequences from Septoria, particularly, *Septoria nodorum* and *Septoria tritici*; Mycosphaerella, particularly *Mycosphaerella fijiensis* and *Mycosphaerella musicola*; Pseudocercosphorella, particularly *Pseudocercosporella herpotrichoides*, more particularly for the W-strain and the R-strain of *Pseudocercosporella herpotrichoides*, Fusarium, particularly *F. graminearum, F. culmorum, F. moniliforme* and *Microdochium nivale*. Such ITS DNA sequences as well as primers of interest are given in SEQ ID NO: 1–47 and SEQ ID NO.: 50–86. The sequences find use in the PCR-based identification of the pathotypes of interest.

Methods for the use of the primer sequences of the invention in PCR analysis are well known in the art. For example, see U.S. Pat. Nos. 4,683,195 and 4,683,202 as well as Schlesser et al. (1991) *Applied and Environ. Microbiol.* 57:553–556. See also, Nazar et al. (1991; *Physiol. and Molec. Plant Pathol.* 39: 1–11) which used PCR amplification to exploit differences in the ITS regions of *Verticillium albo-atrum* and *Verticillium dahliae* and therefore distinguish between the two species; and Johanson and Jeger (1993; *Mycol. Res.* 97: 670–674) who used similar techniques to distinguish the banana pathogens *Mycosphaerella fijiensis* and *Mycospharella musicola.*

The ITS DNA sequences of the invention can be cloned from fungal pathogens by methods known in the art. In general, the methods for the isolation of DNA from fungal isolates are known. See, Raeder & Broda (1985) *Letters in Applied Microbiology* 2:17–20; Lee et al. (1990) *Fungal Genetics Newsletter* 35:23–24; and Lee and Taylor (1990) In: *PCR Protocols: A Guide to Methods and Applications*, Innes et al. (Eds.); pages 282–287.

Alternatively, the ITS regions of interest can be determined by PCR amplification. Primers to amplify the entire ITS region were designed according to White et al. (1990;

In: PCR Protocols; Eds.: Innes et al. pages 315–322) and the amplified ITS sequence was subcloned into the pCRII cloning vector. The subcloned sequence included the left-hand ITS (ITS1), the righthand ITS (ITS2) as well as the centrally located 5.8S rRNA gene. This was undertaken for *Septoria nodorum* and *Septoria tritici*, numerous Pseudocercosporella isolates and *Mycosphaerella fijiensis, Mycosphaerella musicola, Septoria avenae triticea, F graminearum, F. culmorum, F. moniliforme* and *Microdochium nivale.*

The ITS sequences were determined and within each pathogen group the sequences were compared to locate divergences which might be useful to test in PCR to distinguish the different species and/or strains. The sequences of the ITS regions which were determined are shown as Sequence ID's 1 to 6, 47, and 82–86 and also in FIGS. 1, 2 and 3. From the identification of divergences numerous primers were synthesized and tested in PCR-amplification. Templates used for PCR-amplification testing were firstly purified pathogen DNA, and subsequently DNA isolated from infected host plant tissue. Thus it was possible to identify pairs of primers which were diagnostic i.e. which identified one particular pathogen species or strain but not another species or strain of the same pathogen. Preferred primer combinations are able to distinguish between the different species or strains in infected host tissue i.e. host tissue which has previously been infected with a specific pathogen species or strain.

This invention provides numerous primer combinations which fulfill this criterion for different Septoria, Mycosphaerella, and Fusarium species and different strains of Pseudocercosporella. The primers of the invention are designed based on sequence differences among the fungal ITS regions. A minimum of one base pair difference between sequences can permit design of a discriminatory primer. Primers designed to a specific fungal DNA's ITS region can be used in combination with a primer made to a conserved sequence region within the ribosomal DNA's coding region to amplify species-specific PCR fragments. In general, primers should have a theoretical melting temperature between about 60 to about 70 degree C to achieve good sensitivity and should be void of significant secondary structure and 3' overlaps between primer combinations. Primers are generally at least about 5 to about 10 nucleotide bases.

The usefulness of cloned ITS sequences for the selection of primers for diagnostic purposes is largely due to their rapid evolutionary divergence. For example, W-type and R-type isolates of the pathogen Pseudocercosporella herpotrichoides were found to have divergent ITS sequences from which diagnostic primers were developed. However, the rapid divergence within the ITS sequence is apparent from the observation that two different sequence variants of the W-type were identified. The sequence identity within the W-type was 99.4%, whereas that between W and R-types was 98.6% suggesting a closer evolutionary relationship between the two W variants than was found between the W and the R-types. This closer relationship is also apparent from their similar host pathogenicity of the two isolates with divergent ITS sequences.

In addition to developing primers from ITS-derived sequences for PCR diagnosis of fungal isolates, the invention also encompasses the identification of primers from RAPD primer libraries which can distinguish between *Septoria nodorum* and *Septoria tritici* when used in PCR. The primers screened are commercially available and were obtained from Operon Technologies Incorporated (Alameda, Calif.). Screening on Septoria genomic DNA identified two primers which were able to detect only *S. tritici* and three which were able to detect only *S. nodorum.*

The present invention lends itself readily to the preparation of "kits" containing the elements necessary to carry out the process. Such a kit may comprise a carrier being compartmentalized to receive in close confinement therein one or more container means, such as tubes or vials. One of said container means may contain unlabeled or detectably labeled DNA primers. The labeled DNA primers may be present in lyophilized form, or in an appropriate buffer as necessary. One or more container means may contain one or more enzymes or reagents to be utilized in PCR reactions. These enzymes may be present by themselves or in admixtures, in lyophilized form or in appropriate buffers.

Finally, the kit may contain all of the additional elements necessary to carry out the technique of the invention, such as buffers, extraction reagents, enzymes, pipettes, plates, nucleic acids, nucleoside triphosphates, filter paper, gel materials, transfer materials, autoradiography supplies, and the like.

The examples below show, without limitation, typical experimental protocols which can be used in the isolation of ITS sequences, the selection of suitable primer sequences, the testing of primers for selective and diagnostic efficacy, and the use of such primers for disease and fungal isolate detection. Such examples are provided by way of illustration and not by way of limitation.

EXAMPLES

Example 1

Fungal isolates and genomic DNA extraction

Viable fungal isolates of *S. nodorum, S. tritici, S. passerini, S. glycines, Pseudocercosporella herpotrichoides, Pseudocercosporella aestiva, Mycosphaerella citri, Mycosphaerella graminicola, Mycosphaerella fijiensis* and *Mycosphaerella musicola* were obtained from the American Type Culture Collection. *Fusarium culmorum* and *Fusarium graminearum* isolates were obtained from Dr. Paul Nelson from Penn State University. An isolate of *Michrodochium nivale* (syn. *Fusarium nivale*) was received from Ciba-Basel and an isolate of *Fusarium moniliforme* was received from Dr. Loral Castor. Fungi were grown in 150 ml potato dextrose broth inoculated with mycelial fragments from PDA (Potato Dextrose Agar) cultures. Cultures were incubated on an orbital shaker at 28° C. for 7–11 days. Mycelia were pelleted by centrifugation and then ground in liquid nitrogen and total genomic DNA extracted using the protocol of Lee and Taylor (1990; In: *PCR Protocols: A Guide to Methods and Applications*; Eds.: Innes et al.; pages 282–287).

Dr. Bruce McDonald from Texas A&M University supplied genomic DNA from ten isolates of *S. nodorum* and nine isolates of *S. tritici*. Dr. Chris Caten of Birmingham University provided six isolates of *Septoria nodorum* purified fungal DNA. Purified genomic DNA from 12 isolates of *Pseudocercosporella herpotrichoides* was obtained from Dr. Paul Nicholson of the John Innes Centre, Norwich, UK. Six of these isolates are of the W-type; the other six isolates are of the R-type. These isolates were typed based on pathogenicity and RFLP studies. Andrea Johanson of the Natural Resources Institute supplied genomic DNA of six isolates of *M. musicola*, six isolates of *M. fijiensis* and a single isolate of *Mycosphaerella musae.* Purified genomic DNA from *Septoria avenae* f. sp. *triticea* ATCC#26380 was supplied by Dr. Peter Ueng from the USDA at Beltsville, Md.

TABLE 1

Source of Test Isolates

| Isolate | Species | Origin | Source |
|---|---|---|---|
| ATCC#24425 | *S. nodorum* | Montana | ATCC[1] |
| XA1.1 | *S. nodorum* | Texas | B. McDonald[2] |
| Xa5A.2 | *S. nodorum* | Texas | B. McDonald |
| YA3.1 | *S. nodorum* | Texas | B. McDonald |
| XD2.1 | *S. nodorum* | Texas | B. McDonald |
| YB2.2 | *S. nodorum* | Texas | B. McDonald |
| 93HBh6a | *S. nodorum* | Oregon | B. McDonald |
| 93A3a | *S. nodorum* | Oregon | B. McDonald |
| 93AYa | *S. nodorum* | Oregon | B. McDonald |
| 93HBh8a | *S. nodorum* | Oregon | B. McDonald |
| 93C5a | *S. nodorum* | Oregon | B. McDonald |
| ATCC#26517 | *S. tritici* | Minnesota | ATCC |
| BS3 | *S. nodorum* | Ireland | C. Caten[3] |
| BS6 | *S. nodorum* | Ireland | C. Caten |
| BS175 | *S. nodorum* | England | C. Caten |
| BS425 | *S. nodorum* | England | C. Caten |
| alpha'5 | *S. nodorum* | France | C. Caten |
| m300 | *S. nodorum* | England | C. Caten |
| TKV2a | *S. tritici* | Turkey | B. McDonald |
| SYK2 | *S. tritici* | Syria | B. McDonald |
| ISZC36.2 | *S. tritici* | Israel | B. McDonald |
| CNRC4a.1 | *S. tritici* | Canada | B. McDonald |
| ALA1a | *S. tritici* | Algeria | B. McDonald |
| ETK1 | *S. tritici* | Ethiopia | B. McDonald |
| GEB2a.1 | *S. tritici* | Germany | B. McDonald |
| UK92D2 | *S. tritici* | United Kingdom | B. McDonald |
| DNB1a | *S. tritici* | Denmark | B. McDonald |
| ATCC#38699 | *S. glycines* | Illinois | ATCC |
| ATCC#22585 | *S. passerini* | Minnesota | ATCC |
| ATCC#42040 | *P. herpotrichoides-wheat* | | ATCC |
| ATCC#62012 | *P. aestiva* | Germany | ATCC |
| ATCC#60972 | *P. herp. var. herp.*-barley | Germany | ATCC |
| W1 | *P. herpotrichoides* | United Kingdom | P. Nicholson[4] |
| W2 | *P. herpotrichoides* | United Kingdom | P. Nicholson |
| W3 | *P. herpotrichoides* | United Kingdom | P. Nicholson |
| W4 | *P. herpotrichoides* | United Kingdom | P. Nicholson |
| W5 | *P. herpotrichoides* | New Zealand | P. Nicholson |
| W6 | *P. herpotrichoides* | Italy | P. Nicholson |
| R1 | *P. herpotrichoides* | Belgium | P. Nicholson |
| R2 | *P. herpotrichoides* | New Zealand | P. Nicholson |
| R3 | *P. herpotrichoides* | Germany | P. Nicholson |
| R4 | *P. herpotrichoides* | Sweden | P. Nicholson |
| R5 | *P. herpotrichoides* | United Kingdom | P. Nicholson |
| R6 | *P. herpotrichoides* | United Kingdom | P. Nicholson |
| ATCC#22116 | *M. fijiensis* | Philippines | ATCC |
| ATCC#22115 | *M. musicola* | Philippines | ATCC |
| ATCC#24046 | *M. citri* | Florida | ATCC |
| ATCC#62714 | *M. graminicola* | Montana | ATCC |
| PA92 | *M. fijiensis* | Panama | A. Johanson[5] |
| PNG291 | *M. fijiensis* | Papua New Guinea | A. Johanson |
| GH6-3 | *M. fijiensis* | Ghana | A. Johanson |
| TG120 | *M. fijiensis* | Tonga | A. Johanson |
| HSB4 | *M. fijiensis* | Honduras | A. Johanson |
| RT689 | *M. fijiensis* | Rarotonga (Cook Is.) | A. Johanson |
| CR548 | *M. musicola* | Costa Rica | A. Johanson |
| CM61 | *M. musicola* | Cameroon | A. Johanson |
| CU823 | *M. musicola* | Cuba | A. Johanson |
| MQ103 | *M. musicola* | Martinique | A. Johanson |
| CI31 | *M. musicola* | Ivory Coast | A. Johanson |
| CB90 | *M. musicola* | Colombia | A. Johanson |
| BD1-4 | *M. musae* | Barbados | A. Johanson |
| ATCC#44234 | *Ceratobasidium cereale* | Netherlands | ATCC |
| ATCC#11404 | *Drechslera sorokiniana* | Minnesota | ATCC |
| R-5126 | *F. culmorum* | Minnesota | P. Nelson[6] |
| R-5106 | *F. culmorum* | Michigan | P. Nelson |
| R-5146 | *F. culmorum* | Finland | P. Nelson |

TABLE 1-continued

Source of Test Isolates

| Isolate | Species | Origin | Source |
|---|---|---|---|
| R-8417 | *F. graminearum* | Italy | P. Nelson |
| R-8422 | *F. graminearum* | Canada | P. Nelson |
| R-8546 | *F. graminearum* | Bulgaria | P. Nelson |
| 4551 | *F. moniliforme* | Indiana | L. Castor[7] |
| 92 | *M. nivale* | — | Ciba Basel[8] |
| ATCC#26380 | *S. avenae* f.sp.*triticea* | Minnesota | P. Ueng[9] |

[1]American Type Culture Collection, Rockville, Maryland USA
[2]Dr. Bruce McDonald, Texas A&M University, USA
[3]Dr. Chris Caten, Birmingham University, UK
[4]Dr. Paul Nicholson, John Innes Centre, UK
[5]Dr. Andrea Johanson, Natural Resources Institute, UK
[6]Dr. Paul Nelson, Penn State University
[7]Dr. Loral Castor, Ciba Seeds Research, Bloomington, Illinois
[8]Ciba-Geigy Limited, Basel, Switzerland
[9]Dr. Peter Ueng, USDA, Beltsville, Maryland

Example 2

Isolation of the internal transcribed spacer (ITS) regions

The approximately 550 bp internal transcribed spacer region fragments were PCR amplified from 25 ng of genomic DNA isolated from *S. nodorum* (ATCC#24425), *S. tritici* (ATCC#26517), *Pseudocercosporella herpotrichoides* isolates R1, R2, W2 and W5, *M. fijiensis* (ATCC#22115) and *M. musicola* (ATCC#22115) using 50 pmol of primers ITS1 (5'-TCCGTAGGTGAACCTGCGG-3'; SEQ ID NO: 38) and ITS4 (5'-TCCTCCGCTTATTGATATGC-3'; SEQ ID NO:41). PCRs were performed as described in EXAMPLE 4 except that reactions were done in 100 μl and annealing was done at of 50° C. The ITS fragments were purified by isopropanol precipitation according to Maniatis et al. (1982; *Molecular Cloning*; Eds.: Maniatis et al.; pages 461–462). The DNA was resuspended in 50 μl $dH_2O$ and cloned using the Invitrogen Corporation's (San Diego, Calif.) TA Cloning Kit (part no. K2000-01) using the pCRII cloning vector. The DNA sequences of the ITS regions were determined by the dideoxy method using the Applied Biosystems (Foster City, Calif.) automated sequencer model 373A with the primers ITS1 (see sequence above), ITS2 (5'-GCTGCGTTCTTCATCGATGC-3'; SEQ ID NO:39), ITS4 (see sequence above) and the M13 universal -20 (5'-GTAAAACGACGGCCAGT-3'; SEQ ID NO:48) and Reverse (5'-AACAGCTATGACCATG-3'; SEQ ID NO:49) primers. The ITS primers ITS1 (SEQ ID NO:38), ITS2 (SEQ ID NO:39), ITS3 (SEQ ID NO:40), and ITS4 (SEQ ID NO:41) used for cloning the ITS regions are detailed in White et al. (1990; In: PCR Protocols; Eds.: Innes et al. pages 315–322).

In addition, the internal transcribed spacer regions were PCR amplified from 25 ng of genomic DNA from *S. avenae* f.sp. *triticea, M. nivale, F. moniliforme* (#4551), *F. graminearum* isolates R-8417, R-8546 and R-8422 and F culmorum isolates R-5126, R-5106 and R-5146. PCR products were purified using Promega's Wizard DNA Clean-up kit (Madison, Wis.). The DNA sequences of the ITS regions were determined as described above using the ITS1 (SEQ ID NO:38), ITS2 (SEQ ID NO:39), ITS3 (SEQ ID NO:40) and ITS4 (SEQ ID NO:41) primers. Sequencing reactions were combined with the three isolates of *F. culmorum* and *F. graminearum* to generate a consensus sequence for *F. culmorum* and *F. graminearum.*

Example 3

DNA extraction from wheat and banana leaves

DNA was extracted from wheat leaves using a modified version of the Rapid DNA Extraction protocol from the MicroProbe Corporation's (Garden Grove, Calif.) IsoQuick Nucleic Acid Extraction Kit (cat# MXT-020-100). Typical yields were 5–10 μg of total DNA from 0.2 g of leaf tissue. Approximately 100 ng of total DNA were used in each PCR assay.

Modified Rapid DNA Extraction:

Before using kit for the first time, the entire contents of Reagent 2A (20×Dye Concentrate) were added to Reagent 2 (Extraction Matrix).

(1) Approximately 0.2 g of leaf sample were added to a 1.5 ml eppendorf tube containing 50 μl sample buffer A and 50 μl #1 lysis solution. The leaf sample was ground with a Kontes pestle.

(2) Reagent 2 (Extraction Matrix) was shaken vigorously. 350 μl of reagent 2 were added to the sample lysate.

(3) 200 μl of Reagent 3 were added (Extraction Buffer) to the sample. The sample was vortexed 20 sec.

(4) Microcentrifugation at 12,000×g for 5 min.

(5) The aqueous phase (upper layer) was transferred to a new microcentrifuge tube. This volume was typically about 200 μl.

(6) 0.1×the volume of the aqueous phase of Reagent 4 (Sodium Acetate) to the aqueous phase sample.

(7) An equal volume of isopropanol was added to the aqueous phase sample followed by vortexing.

(8) Microcentrifugation at 12,000×g for 10 min.

(9) The supernatant was discarded without disturbing the nucleic acid pellet. 0.5 ml of −20° C. 70% ethanol was added to the pellet. The tube was vortexed to mix.

(10) Microcentrifugation at 12,000×g for 5 min.

(11) The supernatant was discarded and the pellet was allowed to dry.

(12) The nucleic acid pellet was dissolved in 50 μl Reagent 5 (RNase-free water).

Example 4

Polymerase chain reaction amplification

Polymerase chain reactions were performed with the GeneAmp Kit from Perkin-Elmer/Cetus (Norwalk, Conn.; part no. N808-0009) using 50 mM KCl, 2.5 mM $MgCl_2$, 10 mM Tris-HCl, pH8.3, containing 100 μM of each TTP, DATP, dCTP, and dGTP, 50 μM primer, 2.5 units of Taq polymerase and 25 ng of genomic DNA in a final volume of 50 μl. Reactions were run for 30 cycles of 15 s at 94° C., 15 s at 50° C., 60° C. or 70° C., and 45 s at 72° C. in a Perkin-Elmer/Cetus Model 9600 thermal cycler. The products were analyzed by loading 20 μl of each PCR sample on a 1.1–1.2% agarose gel and electrophoresed.

Example 5

Synthesis and Purification of Oligonucleotides

Oligonucleotides (primers) were synthesized on an Applied Biosystems 380A DNA synthesizer using B-cyanothyl-phosphoramidite chemistry.

Example 6

Selection of species-specific primers

The ITS sequences of *S. nodorum, S. tritici, P. herpotrichoides* strains R and W, *M. fijiensis* and *M. musicola* were aligned (FIG. 1). The ITS sequences of *S. nodorum* and *S. avenae. triticea* were aligned (FIG. 2). An alignment was also made of the ITS sequences from *F. graminearum, F. culmorum, F. moniliforme* and *M. nivale* (FIG. 3). Sets of primers were synthesized according to EXAMPLE 5 based on analysis of the aligned sequences. Primers were designed to regions containing the greatest differences in sequence among the fungal species for FIGS. 1–2. In FIG. 3, primers were designed to regions of highest homology within the ITS for Fusarium. In addition, the published ribosomal gene-specific primers ITS1 (SEQ ID NO:38), ITS2 (SEQ ID NO:39), ITS3 (SEQ ID NO:40) and ITS4 (SEQ ID NO:41) (White et al., 1990; In: PCR Protocols; Eds.: Innes et al. pages 315–322) were synthesized for testing in combination with the primers specific for the ITS region.

TABLE 2

Primer Design for Fungal Detection

| Primer Template | Primer Name | Primer Sequence | |
|---|---|---|---|
| *S. nodorum* | JB433 | 5' ACACTCAGTAGTTTACTACT 3' | (SEQ ID NO:7) |
| *S. nodorum* | JB434 | 5' TGTGCTGCGCTTCAATA 3' | (SEQ ID NO:8) |
| *S. nodorum* | JB525 | 5' GCGACTTGTGCTGCGCTTCAATA 3' | (SEQ ID NO:9) |
| *S. nodorum* | JB527 | 5' CATTACACTCAGTAGTTTACTACT 3' | (SEQ ID NO:10) |
| *S. tritici* | JB445 | 5' CTGCGTCGGAGTTTACG 3' | (SEQ ID NO:11) |
| *S. tritici* | JB446 | 5' CGAGGCTGGAGTGGTGT 3' | (SEQ ID NO:12) |
| *S. tritici* | JB526 | 5' CCCAGCGAGGCTGGAGTGGTGT 3' | (SEQ ID NO:13) |
| *P. herp.* | JB536 | 5' CTGGGGGCTACCCTACTTGGTAG 3' | (SEQ ID NO:14) |
| *P. herp.* | JB537 | 5' GGGGGCTACCCTACTTGGTAG 3' | (SEQ ID NO:15) |
| *P. herp.* | JB538 | 5' ACTTGGTAGGGTTTAGAGTCGTCA 3' | (SEQ ID NO:16) |
| *P. herp.* | JB539 | 5' CTTCGGTAAGGTTTAGAGTCGTCG 3' | (SEQ ID NO:17) |
| *P. herp.* | JB540 | 5' GGGGGCCACCCTACTTCGGTAA 3' | (SEQ ID NO:18) |
| *P. herp.* | JB541 | 5' CCACTGATTTTAGAGGCCGCGAG 3' | (SEQ ID NO:19) |

TABLE 2-continued

Primer Design for Fungal Detection

| Primer Template | Primer Name | Primer Sequence | |
|---|---|---|---|
| *P. herp.* | JB542 | 5' CCACTGATTTTAGAGGCCGCGAA 3' | (SEQ ID NO:20) |
| *P. herp.* | JB543 | 5' CCTGTAAAAAATTGGGGGTTA 3' | (SEQ ID NO:21) |
| *P. herp.* | JB544 | 5' CCTGTAAAAAATTGGGGGTTG 3' | (SEQ ID NO:22) |
| *M. fijiensis* | JB547 | 5' ATTACCGAGTGAGGGCTCACGC 3' | (SEQ ID NO:23) |
| *M. fijiensis* | JB548 | 5' GTTGCTTCGGGGGCGACCTG 3' | (SEQ ID NO:24) |
| *M. fijiensis* | JB442 | 5' TCGGGGGCGACCTGCCG 3' | (SEQ ID NO:25) |
| *M. fijiensis* | JB443 | 5' CCGGAGGCCGTCTA 3' | (SEQ ID NO:26) |
| *M. fijiensis* | JB545 | 5' CCACAACGCTTAGAGACGGACAG 3' | (SEQ ID NO:27) |
| *M. fijiensis* | JB546 | 5' CACCCGCACTCCGAAGCGAATT 3' | (SEQ ID NO:28) |
| *M. fijiensis* | JB549 | 5' GATCCGAGGTCAACCTTTGAATAA 3' | (SEQ ID NO:29) |
| *M. fijiensis* | JB444 | 5' GGTCAACCTTTGAATAA 3' | (SEQ ID NO:30) |
| *M. musicola* | JB451 | 5' CCTTTGTGAACCACACCT 3' | (SEQ ID NO:31) |
| *M. musicola* | JB440 | 5' CTGCCGGCGAACTT 3' | (SEQ ID NO:32) |
| *M. musicola* | JB449 | 5' ACCCTGCCGGCGAACTT 3' | (SEQ ID NO:33) |
| *M. musicola* | JB448 | 5' GCGACCCTGCCGGCGAAC 3' | (SEQ ID NO:34) |
| *M. musicola* | JB441 | 5' TAGCCGGGAGACTTGG 3' | (SEQ ID NO:35) |
| *M. musicola* | JB450 | 5' TCTGCGTCGGAGTTCC 3' | (SEQ ID NO:36) |
| *M. musicola* | JB452 | 5' CCGCGCTCCGGAGCGAAC 3' | (SEQ ID NO:37) |
| 18S rDNA | ITS1 | 5' TCCGTAGGTGAACCTGCGG 3' | (SEQ ID NO:38) |
| 5.8S rDNA | ITS2 | 5' GCTGCGTTCTTCATCGATGC 3' | (SEQ ID NO:39) |
| 5.8S rDNA | ITS3 | 5' GCATCGATGAAGAACGCAGC 3' | (SEQ ID NO:40) |
| 25S rDNA | ITS4 | 5' TCCTCCGCTTATTGATATGC 3' | (SEQ ID NO:41) |
| *S. nodorum* | JB563 | 5' CTTGCCTGCCGGTTGGACAAATT 3' | (SEQ ID NO:50) |
| *S. nodorum* | JB564 | 5' CTCAGTAGTTTACTACTGTAAAAGG 3' | (SEQ ID NO:51) |
| *S. nodorum* | JB565 | 5' CTTCTGGACGCAAGTGTTTGTTAC 3' | (SEQ ID NO:52) |
| *Fusarium* spp. | JB566 | 5' GTTTTTAGTGGAACTTCTGAGT 3' | (SEQ ID NO:53) |
| *Fusarium* spp. | JB567 | 5' CGCAGGAACCCTAAACTCT 3' | (SEQ ID NO:54) |
| *Fusarium* spp. | JB568 | 5' GCCCGCCGCAGG 3' | (SEQ ID NO:55) |
| *Fusarium* spp. | JB569 | 5' RTWWTTWRTGGAMYYTCTGAGT 3' | (SEQ ID NO:56) |
| *Fusarium* spp. | JB570 | 5' TATGTTGCCTCGGCGG 3' | (SEQ ID NO:57) |
| *Fusarium* spp. | JB571 | 5' TAACGATATGTAAATTACTACGCT 3' | (SEQ ID NO:58) |
| *Fusarium* spp. | JB572 | 5' AAGTTGGGGTTTAACGGC 3' | (SEQ ID NO:59) |
| *Fusarium* spp. | JB573 | 5' AGCGAGCCCGCCAC 3' | (SEQ ID NO:60) |
| *Fusarium* spp. | JB574 | 5' CCATTGTGAACGTTACCTATAC 3' | (SEQ ID NO:61) |
| *Fusarium* spp. | JB575 | 5' CGACCAGAGCGAGATGTA 3' | (SEQ ID NO:62) |
| *Fusarium* spp. | JB576 | 5' GTGAACATACCTTATGTTGCC 3' | (SEQ ID No:63) |

TABLE 2-continued

Primer Design for Fungal Detection

| Primer Template | Primer Name | Primer Sequence | |
|---|---|---|---|
| *Fusarium* spp. | JB577 | 5' GTTGCCTCGGCGGATC 3' | (SEQ ID NO:64) |
| *Fusarium* spp. | JB578 | 5' CCGCGACGATTACCAG 3' | (SEQ ID NO:65) |

NOTE: *Fusarium* supp. includes *F. graminearum, F. culmorum, F. moniliforme* and *Michrodochium nivale* (syn. *F. nivale* ).

Example 7

Selection of Random Amplified Polymorphic DNA (RAPD) primers

Two RAPD primer libraries (kits B and E) of twenty oligonucleotides each were purchased from Operon Technologies Incorporated (Alameda, Calif.). The primers were tested for their ability to differentiate purified genomic DNA of *S. nodorum, S. tritici, M. fijiensis* and *M. musicola*. The PCR conditions were essentially the same as described in EXAMPLE 4 except the number of PCR cycles was increased to 35, the annealing temperature was 30° C. and only 5 picamoles of each primer were used. Five RAPD primers were identified that differentiate purified genomic DNA of *S. nodorum, S. tritici, M. fijiensis* and *M. musicola*. Primers OPB-12 and OPE-6 produced a single fragment when amplified with *S. tritici* genomic DNA. Primers OPE-12, OPB-19 and OPE-15 produced single fragments from *S. nodorum* genomic DNA. Primers OPB-12 and OPE-6 did not produce any amplification products from *S. nodorum M. fijiensis* and *M. musicola* genomic DNA. Primers OPE-12, OPB-19 and OPE-15 did not amplify any fragments from genomic *S. tritici, M. fijiensis* or *M. musicola* DNA.

TABLE 3

RAPD Primers for *Septoria* Diagnosis

| Source of template DNA | Primer | Sequence of primer | Approximate size of amplified fragment |
|---|---|---|---|
| *S. tritici* | OPB-12 | 5'-CCTTGACGCA-3' (SEQ ID NO: 42) | 1.3 kb |
| *S. tritici* | OPE-6 | 5'-AAGACCCCTC-3' (SEQ ID NO: 43) | 1.0 kb |
| *S. nodorum* | OPE-12 | 5'-TTATCGCCCC-3' (SEQ ID NO: 44) | 2.2 kb |
| *S. nodorum* | OPB-19 | 5'-ACCCCCGAAG-3' (SEQ ID NO: 45) | 1.1 kb |
| *S. nodorum* | OPE-15 | 5'-ACGCACAACC-3' (SEQ ID NO: 46) | 1.3 kb |

Example 8

Determination of primer specificity to purified fungal genomic DNA

PCRs were performed according to EXAMPLE 4 using different primer combinations in an attempt to amplify a single species-specific fragment. Species-specific PCR amplification products were produced from primers designed from the ITS region between the 18S and 25S ribosomal DNA subunits of each fungal strain of interest.

TABLE 4

ITS-derived diagnostic PCR primers

| Source of template DNA | 5'Primer | 3'Primer | Approximate size of amplified fragment |
|---|---|---|---|
| *Septoria nodorum* | JB433 (SEQ ID NO:7) | JB434 (SEQ ID NO:8) | 448bp |
| | JB433 (SEQ ID NO:7) | ITS4 (SEQ ID NO:41)(JB415) | 553bp |
| | ITS1 (SEQ ID NO:38)(JB410) | JB434 (SEQ ID NO:8) | 478bp |
| | ITS3 (SEQ ID NO:40)(JB414) | JB434 (SEQ ID NO:8) | 232bp* |
| | JB527 (SEQ ID NO:10) | JB525 (SEQ ID NO:9) | 458bp |
| | JB564 (SEQ ID NO:51) | JB565 (SEQ ID NO:52) | 480bp |
| | JB563 (SEQ ID NO:50) | JB565 (SEQ ID NO:52) | 368bp |
| *Septoria tritici* | JB445 (SEQ ID NO:11) | ITS4 (SEQ ID NO:41)(JB415) | 407bp |
| | ITS1 (SEQ ID NO:38)(JB410) | JB446 (SEQ ID NO:12) | 345bp |

TABLE 4-continued

ITS-derived diagnostic PCR primers

| Source of template DNA | 5'Primer | 3'Primer | Approximate size of amplified fragment |
|---|---|---|---|
| | ITS3 (SEQ ID NO:40)(JB414) | JB446 (SEQ ID NO:12) | 143bp* |
| | JB445 (SEQ ID NO:11) | JB446 (SEQ ID NO:12) | 204bp |
| * | | | |
| *M. fijiensis* | JB443 (SEQ ID NO:26) | ITS4 (SEQ ID NO:41)(JB415) | 418bp |
| | ITS1 (SEQ ID NO:38)(JB410) | JB444 (SEQ ID NO:30) | 482bp |
| | JB443 (SEQ ID NO:26) | JB444 (SEQ ID NO:30) | 366bp* |
| | ITS3 (SEQ ID NO:40)(JB414) | JB444 (SEQ ID NO:30) | 281bp |
| | ITS1 (SEQ ID NO:38)(JB410) | JB549 (SEQ ID NO:29) | 489bp |
| *M. musicola* | JB449 (SEQ ID NO:33) | ITS4 (SEQ ID NO:41)(JB415) | 430bp |
| | JB448 (SEQ ID NO:34) | ITS4 (SEQ ID NO:41)(JB415) | 449bp* |
| | JB448 (SEQ ID NO:34) | ITS2 (SEQ ID NO:39)(JB411) | 138bp* |
| | JB450 (SEQ ID NO:36) | ITS4 (SEQ ID NO:41)(JB415) | 390bp* |
| *P. herpotrichoides* | JB536 (SEQ ID NO:14) | JB541 (SEQ ID NO:19) | 415bp$^+$ |
| | JB536 (SEQ ID NO:14) | JB543 (SEQ ID NO:21) | 502bp$^+$ |
| | JB537 (SEQ ID NO:15) | JB541 (SEQ ID NO:19) | 413bp$^+$ |
| | JB537 (SEQ ID NO:15) | JB543 (SEQ ID NO:21) | 500bp$^+$ |
| | JB538 (SEQ ID NO:16) | JB541 (SEQ ID NO:19) | 401bp$^+$ |
| | JB538 (SEQ ID NO:16) | JB543 (SEQ ID NO:21) | 488bp$^+$ |
| | JB536 (SEQ ID NO:14) | ITS4 (SEQ ID NO:41)(JB415) | 560bp$^+$ |
| | JB537 (SEQ ID NO:15) | ITS4 (SEQ ID NO:41)(JB415) | 558bp$^+$ |
| | JB538 (SEQ ID NO:16) | ITS4 (SEQ ID NO:41)(JB415) | 546bp$^+$ |
| | ITS1 (SEQ ID NO:38)(JB410) | JB541 (SEQ ID NO:19) | 482bp$^+$ |
| | ITS1 (SEQ ID NO:38)(JB410) | JB543 (SEQ ID NO:21) | 569bp$^+$ |
| | ITS1 (SEQ ID NO:38)(JB410) | JB542 (SEQ ID NO:20) | 482bp$^+$ |
| | ITS1 (SEQ ID NO:38)(JB410) | JB544 (SEQ ID NO:22) | 569bp$^{++}$ |
| | JB540 (SEQ ID NO:18) | ITS4 (SEQ ID NO:41)(JB415) | 558bp$^{++}$ |
| | JB539 (SEQ ID NO:17) | ITS4 (SEQ ID NO:41)(JB415) | 545bp$^{++}$ |
| | JB540 (SEQ ID NO:18) | JB542 (SEQ ID NO:20) | 413bp$^{++}$ |
| | JB540 (SEQ ID NO:18) | JB544 (SEQ ID NO:22) | 500bp$^{++}$ |
| | JB539 (SEQ ID NO:17) | JB542 (SEQ ID NO:20) | 400bp$^{++}$ |
| | JB539 (SEQ ID NO:17) | JB544 (SEQ ID NO:22) | 487bp$^{++}$ |
| *Fusarium supp.* | JB566 (SEQ ID NO:53) | ITS4 (SEQ ID NO:41)(JB415) | 430bp$^1$ |
| | JB566 (SEQ ID NO:53) | JB572 (SEQ ID NO:59) | 346bp$^1$ |
| | JB569 (SEQ ID NO:56) | ITS4 (SEQ ID NO:41)(JB415) | 430bp$^1$ |
| | JB569 (SEQ ID NO:56) | JB572 (SEQ ID NO:59) | 346bp$^1$ |
| | ITS1 (SEQ ID NO:38)(JB410) | JB572 (SEQ ID NO:59) | 485bp$^1$ |
| | JB566 (SEQ ID NO:53) | JB571 (SEQ ID NO:58) | 308bp$^2$ |
| | JB569 (SEQ ID NO:56) | JB571 (SEQ ID NO:58) | 308bp$^2$ |
| | JB570 (SEQ ID NO:57) | ITS4 (SEQ ID NO:41)(JB415) | 501bp$^2$ |
| | JB570 (SEQ ID NO:57) | JB571 (SEQ ID NO:58) | 379bp$^2$ |
| | JB570 (SEQ ID NO:57) | JB578 (SEQ ID NO:65) | 395bp$^2$ |
| | JB567 (SEQ ID NO:54) | ITS4 (SEQ ID NO:41)(JB415) | 450bp$^2$ |
| | JB567 (SEQ ID NO:54) | JB571 (SEQ ID NO:58) | 328bp$^2$ |
| | JB567 (SEQ ID NO:54) | JB572 (SEQ ID NO:59) | 366bp$^2$ |
| | JB567 (SEQ ID NO:54) | JB578 (SEQ ID NO:65) | 344bp$^2$ |
| | JB568 (SEQ ID NO:55) | ITS4 (SEQ ID NO:41)(JB415) | 459bp$^2$ |
| | JB568 (SEQ ID NO:55) | JB571 (SEQ ID NO:58) | 337bp$^2$ |
| | JB568 (SEQ ID NO:55) | JB572 (SEQ ID NO:59) | 375bp$^2$ |
| | JB576 (SEQ ID NO:63) | ITS4 (SEQ ID NO:41)(JB415) | 510bp$^2$ |
| | JB576 (SEQ ID NO:63) | JB578 (SEQ ID NO:65) | 404bp$^2$ |
| | JB577 (SEQ ID NO:64) | ITS4 (SEQ ID NO:41)(JB415) | 495bp$^2$ |
| | JB577 (SEQ ID NO:64) | JB571 (SEQ ID NO:58) | 373bp$^2$ |
| | JB577 (SEQ ID NO:64) | JB578 (SEQ ID NO:65) | 389bp$^2$ |
| | ITS1 (SEQ ID NO:38)(JB410) | JB571 (SEQ ID NO:58) | 447bp$^2$ |
| | ITS1 (SEQ ID NO:38)(JB410) | JB578 (SEQ ID NO:65) | 463bp$^2$ |
| | ITS1 (SEQ ID NO:38)(JB410) | JB575 (SEQ ID NO:62) | 479bp$^2$ |
| *M. nivale* | JB569 (SEQ ID NO:56) | JB575 (SEQ ID NO:62) | 340bp |
| | JB567 (SEQ ID NO:54) | JB575 (SEQ ID NO:62) | 360bp |
| | JB574 (SEQ ID NO:61) | ITS4 (SEQ ID NO:41)(JB415) | 520bp |
| | JB574 (SEQ ID NO:61) | JB572 (SEQ ID NO:59) | 436bp |

*Primer combination amplified some fragments by false priming but none were the size of the desired fragment.
$^+$Primers amplified the correct size fragment from both R-type and W-type of *Pseudocercosporella herpotrichoides*.
$^{++}$Primer combination amplified the correct size fragment from the R-type of *P. herpotrichoides* only.

TABLE 4-continued

ITS-derived diagnostic PCR primers

| Source of template DNA | 5'Primer | 3'Primer | Approximate size of amplified fragment |
|---|---|---|---|

[1]Primer combination amplified the correct size fragment from *F. graminearum, F. culmorum, F. moniliforme* and *M. nivale*.
[2]Primer combination amplified the correct size fragment from *F. graminearum, F. culmorum* and *F. moniliforme*.

Example 9

Determination of primer specificity to plant tissue infected with fungi

Total genomic DNA was isolated from healthy wheat leaves, wheat leaves infected with *S. nodorum*, wheat leaves infected with *S. tritici* and wheat leaves infected with both *S. nodorum* and *S. tritici* using the protocol described in EXAMPLE 3. PCRs were performed as described in EXAMPLE 4 testing the primer combinations listed in EXAMPLE 8 against DNA from the wheat leaves.

The *S. tritici*-specific primer JB446 (SEQ ID NO: 12) and ITS1 (SEQ ID NO:38)(JB410) amplified a 345 bp fragment from purified *S. tritici* DNA, from *S. tritici*-infected wheat leaf tissue and from a wheat leaf sample infected with both *S. tritici* and *S. nodorum*. The primer set did not amplify a diagnostic fragment from healthy wheat leaf tissue nor from *S. nodorum*-infected wheat tissue. Similarly, the *S. tritici*-specific primers JB445 (SEQ ID NO:11) and ITS4 (SEQ ID NO:41)(JB415) amplified a 407 bp fragment from the same tissues as the primer combination JB446 (SEQ ID NO:12) and ITS1 (SEQ ID NO:38)(JB410) and was also diagnostic.

Similarly diagnostic results were obtained with the *S. nodorum*-specific primers JB433 (SEQ ID NO:7) and JB434 (SEQ ID NO:8). The primers amplified a 448 bp fragment from *S. nodorum*-infected wheat tissue, from a wheat leaf sample infested with both *S. nodorum* and *S. tritici*, as well as from purified genomic DNA of *S. nodorum*. The primer combination JB433 (SEQ ID NO:7) and JB434 (SEQ ID NO:8) did not amplify any fragments from healthy wheat tissue, from *S. tritici*-infected wheat tissue or from purified genomic DNA of *S. tritici*. The *S. nodorum*-specific primers JB527 (SEQ ID NO:10) and JB525 (SEQ ID NO:9) amplified a 458 bp fragment from the same genomic DNAs and wheat tissues as the JB433 (SEQ ID NO:7) and JB434 (SEQ ID NO:8) combination.

The *P. herpotrichoides* primer combinations listed in EXAMPLE 8 were PCR tested against the extracts from wheat stems as pbtained in Example 12. PCRs were performed as described in EXAMPLE 4 with the following changes: 35 cycles were run of 94° C. for 15 sec and 70° C. for 45 sec, 1.5–2.5 mM $MgCl_2$ and 200 $\mu$M of each dNTP was used. 1 $\mu$l of wheat extract was used in each PCR.

Primer combination JB537 (SEQ ID NO: 105) and JB541 (SEQ ID NO: 1 9) amplified a 413 bp fragment from wheat extract infected with the W-type pathotype of *P. herpotrichoides*. No amplification products were produced from amplification with healthy wheat extract nor from wheat extract infected with the R-type pathotype of *P. herpotrichoides*.

The primer combination JB539 (SEQ ID NO: 17) and JB544 (SEQ ID NO:22) amplified a 487 bp fragment and primer combination JB540 (SEQ ID NO: 18) and JB542 (SEQ ID NO:20) amplified a 413 bp fragment from R-type infected wheat but not from healthy wheat nor from W-type infected wheat.

Total genomic DNA was also isolated from healthy banana leaves and from banana leaves infected with *M. fijiensis* using the protocol described in EXAMPLE 3. PCRs were performed as described in EXAMPLE 4 testing the *M. fijiensis* primer combinations listed in EXAMPLE 8 against DNA from the banana leaves.

The *M. fijiensis*-specific primer JB549 (SEQ ID NO:29) and ITS1 (SEQ ID NO:38)(JB410) amplified a 489 bp fragment from purified M fijiensis DNA and from *M. fijiensis*-infected banana leaf tissue. The primer set did not amplify a diagnostic fragment from healthy banana leaf tissue. The *M. fijiensis*-specific primer combinations JB443 (SEQ ID NO:26)/ITS4 (SEQ ID NO:41)(JB415) and ITS1 (SEQ ID NO:38)(JB410)/JB444 (SEQ ID NO:30) amplified a 418 bp fragment and a 482 bp fragment, respectively, from the same genomic DNA and banana leaf tissue as the JB549 (SEQ ID NO:29) and ITS1 (SEQ ID NO:38)(JB410) primer combination.

Example 10

Determination of cross-reactivity of species-specific primers with other species and isolates Purified fungal genomic DNAs were obtained as described in EXAMPLE 1 and PCR assayed as described in EXAMPLE 4 using the species-specific primers. Other fungal DNA species and isolates were tested for the species-specific primers ability to cross-react with them.

The *S. tritici*-specific primer JB446 (SEQ ID NO:12) and ITS1 (SEQ ID NO:38)(JB410) amplified a 345 bp fragment from all of the *S. tritici* isolates listed in EXAMPLE 1. There was no cross-reactivity with purified genomic DNA of *S. nodorum, S. glycines* or *S. passerini*. None of these other fungal species produced an amplification product with the *S. tritici*-specific primers.

A 448 bp fragment was amplified from all of the *S. nodorum* isolates listed in EXAMPLE 1 using the *S. nodorum*-specific primers JB433 (SEQ ID NO:7) and JB434 (SEQ ID NO:8). Similarly the *S. nodorum*-specific primers JB527 (SEQ ID NO: 10) and JB525 (SEQ ID NO:9) amplified a 458 bp fragment from all the *S. nosorum* isolates listed in EXAMPLE 1. *S. tritici, S. glycines* and *S. passerini* did not produce any amplification products when assayed with the either of the *S. nodorum*-specific primer sets JB433 (SEQ ID NO:7) and JB434 (SEQ ID NO:8) or JB527 (SEQ ID NO:10) and JB525 (SEQ ID NO:9).

PCRs were run using the conditions described in EXAMPLE 9, the *P. herpotrichoides*-specific primer combinations listed in EXAMPLE 8 against the other fungal DNA species and isolates listed in EXAMPLE 1.

The primer combination JB537 (SEQ ID NO: 15) and JB541 (SEQ ID NO: 19) produced a 413 bp fragment from the W-type *P. herpotrichoides* isolates only when tested against the *P. herpotrichoides* isolates and the following cereal pathogens: *P. aestiva, C. cereale, P. sorokiniana, S. tritici* and *S. nodorum*. The primer combiantion JB539 (SEQ ID NO: 17) and JB544 (SEQ ID NO:22) amplified a 487 bp fragment from the R-type *P. herpotrichoides* isolate only when tested against the same DNAs. The primer combination JB540 (SEQ ID NO: 18) and JB542 (SEQ ID NO:20) produced a 413 bp fragment from the R-type *P. herpotrichoides* isolate only when tested against the same DNAs.

Example 11

Sources of *Pseudocercosporella herpotrichoides*-infected wheat Eyespot-infected wheat stems were received from the stage 1c fungicide screening program of Ciba Basle. Eight day old wheat plants were infected with *P. herpotrichoides* by spraying a conidial suspension ($5\times10^5$ conidia/ml) in 0.2% Tween 20 on the base of the wheat stems. After inoculation, the plants were covered with plastic and incubated for one day at 20° C. and 95–100% relative humidity. The plants were transferred to a growth chamber where they were incubated for four weeks at 12° C. and 60% relative humidity. After this incubation, the plants were moved to a greenhouse and incubated at 18° C. and 60% relative humidity. Wheat plants infected with W-type *P. herpotrichoides* strain 311 were sampled at 8–9 weeks post-infection, while those infected with the R-type strain 308 pathogen were harvested at 9–10 weeks post-infection Example 12

DNA extraction from wheat stems for *P. herpotrichoides* assay

DNA was extracted from wheat stems using the protocol described by Klimyuk et al. (The Plant Journal 3(3) :493–494) with some modifications. A 2 cm wheat stem cut 0.5 cm above the basal culm was placed in 160 μl of 0.25 M NaOH and ground with a Kontes pestle until completely macerated. The sample was boiled for 30 s. 160 μl of 0.25 M HCl and 80 μl of 0.5 M Tris-Cl,pH8.0/0.25% v/v Nonidet P-40 were added to the sample. The sample was boiled for an additional 2 mins., then placed in an ice water bath. 1 μl of extract was used in the PCR assay.

Example 13

Incorporation of diagnostic assays into a quantitative colormetric assay format

The colormetric assay was performed according to Nikiforov et al. (PCR Methods and Applications 3:285–291) with the following changes:

1) 30 μl of the R-type PCR product and 3 M NaCl/20 mM EDTA mixture were added to the capture primer well. 50 μl of the W-type PCR product and 3 M NaCl/20 mM EDTA mixture were used in the hybridization reaction.

2) The exonuclease treatment and hybridization reaction were incubated at 37° C.

3) A 1:1000 dilution of anti-biotin horseradish peroxidase (HRP) monoclonal antibody was used.

4) After a 2 min. incubation with the O-phenylenediamine dihydrochloride (OPD) substrate, 50 μl of 3 N HCl were added to each assay well. 96-well plates were read at 492 nm and referenced at 570 nm using a conventional ELISA plate reader.

The primers listed in Table 5 were synthesized as described in EXAMPLE 5 for testing as capture primers for the colormetric assay.

TABLE 5

Capture Primer Design for Colormetric Assay

| Primer Name | Primer Template | Primer Sequence | |
|---|---|---|---|
| ITS2 | 5.8S rDNA | 5'GCTGCGTTCTTCATCGATGC3' | (SEQ ID NO:39) |
| JB541 | W-type *P. herp.* | 5'CCACTGATTTTAGAGGCCGCGAG3' | (SEQ ID NO:19) |
| JB542 | R-type *P. herp.* | 5'CCACTGATTTTAGAGGCCGCGAA3' | (SEQ ID NO:20) |
| JB538' | W-type *P. herp.* | 5'TGACGACTCTAAACCCTACCA3' | (SEQ ID NO:66) |
| JB539' | R-type *P. herp.* | 5'CGACGACTCTAAACCTTACCG3' | (SEQ ID NO:67) |
| W130 | W-type *P. herp.* | 5'ATTCAAGGGTGGAGGTCTGA3' | (SEQ ID NO:68) |
| R130 | R-type *P. herp.* | 5'ATTCAAGGGTGGAGGTCTGG3' | (SEQ ID NO:69) |
| JB538' | 15 W-type *P. herp.* | 5'CTCTAAACCCTACCA3' | (SEQ ID NO:70) |
| JB539' | 15 R-type *P. herp.* | 5'CTCTAAACCCTACCG3' | (SEQ ID NO:71) |
| JB553 | R & W types | 5'GTGGTCCTCTGGCAG3' | (SEQ ID NO:72) |
| JB554 | R & W types | 5'CTCAACAGCCGAAGC3' | (SEQ ID NO:73) |
| JB555 | W-type *P. herp.* | 5'GGGTGGAGGTCTGA3' | (SEQ ID NO:74) |
| JB556 | R-type *P. herp.* | 5'GGTGGAGGTCTGG3' | (SEQ ID NO:75) |
| JB561 | R-type *P. herp.* | 5'TGGAGGTCTGGACCA3' | (SEQ ID NO:76) |
| JB562 | W-type *P. herp.* | 5'TGGAGGTCTGAACCA3' | (SEQ ID NO:77) |
| JB559 | W-type *P. herp.* | 5'AGGGTGGAGGTCTGA3' | (SEQ ID NO:78) |
| JB560 | R-type *P. herp.* | 5'AGGGTGGAGGTCTGG3' | (SEQ ID NO:79) |

TABLE 5-continued

Capture Primer Design for Colormetric Assay

| Primer Name | Primer Template | Primer Sequence | |
|---|---|---|---|
| JB557 | W-type *P. herp.* | 5'TTCTCCGAGAGGCCT3' | (SEQ ID NO:80) |
| JB558 | R-type *P. herp.* | 5'TTCTCCGAGAGGCCC3' | (SEQ ID NO:81) |

The S. nodorum diagnostic primers JB527 (SEQ ID NO: 10) and JB525 (SEQ ID NO:9) were integrated into the quantitative colormetric assay format. The primer JB527 (SEQ ID NO: 10) was synthesized by Midland Certified Reagent Complany (Midland, Tex.) to contain a biotin label and the 5' end to contain four intemucleotidic phosphorothioate bonds. PCR amplification as described in EXAMPLE 4 using the modified JB527 (SEQ ID NO: 10) and JB525 (SEQ ID NO:9) primers from healthy, low, medium, and highly *S. nodorum*-infected wheat produced no, low, medium and high A492 values, respectively, when assayed colormetrically using the ITS2 (SEQ ID NO:39) primer as the PCR product capture primer.

The *P. herpotrichoides* R-type specific 5' primers, JB539 (SEQ ID NO: 17) and JB540 (SEQ ID NO: 18), and the *P. herpotrichoides* W-type specific 5' primer, JB537 (SEQ ID NO: 15), were also modified to contain a biotin label and four internucleotidic phosphorothioate bonds. A colormetric version of the *P. herpotrichoides* R-type PCR assay was developed using the modified JB540 (SEQ ID NO: 18) primer, JB542 (SEQ ID NO:20) primer and the capture primer JB539'15. The products produced from amplification from R-type infected wheat and from R-type genomic DNA using the modified JB540 (SEQ ID NO: 18) primer and JB542 (SEQ ID NO:20) primer produced positive colormetric values when assayed colormetrically. Positive colormetric values were also obtained by colormetric analysis of the PCR products from amplification using the modified JB537 (SEQ ID NO: 15) primer and W-type specific primer JB541 (SEQ ID NO:19)with W-type infected wheat and W-type genomic DNA when JB538'15 was used as the capture primer. Furthermore, the intensity of the colormetric signal corresponded to the fragment intensity of the PCR product as visualized on an agarose gel.

Previously, the different Septoria species were identifiable by examination under the microscope, and the identification of the different Pseudocercosporella strains has been possible only by pathological tests. Similarly, the unambiguous identification of *Mycosphaerella musicola* and *Mycosphaerella fijiensis* has been difficult, and even the isolation of mature perithecia does not always allow accurate identification (Pons, 1990; In: Sigatoka Leaf Spot Diseases of Banana, Eds. R A Fullerton and R H Stover, International Network for the Improvement of Banana and Plantain, France). Currently immunodiagnostic kits utilizing ELISA technology are routinely used to identify *Septoria tritici, Septoria nodorum, Pseudocercosporella herpotrichoides* and other pathogen, but this technology lacks the accuracy, detection limit and ability to distinguish different isolates of the instant invention. In consequence, the development of a DNA test for the rapid identification of different strains of these fungi offers real advantages not only to fungal taxonomists, but also for disease management and selective fungicide use in the field.

While the present invention has been described with reference to specific embodiments thereof, it will be appreciated that numerous variations, modifications, and further embodiments are possible, and accordingly, all such variations, modifications and embodiments are to be regarded as being within the scope of the present invention.

Deposits

The following deposits were made on Mar. 28, 1994, at Agricultural Research Service, Patent Culture Collection (NRRL), Northern Regional Research Center, 1815 North University Street, Peoria, Ill. 61604, U.S.A.:

1. HB101 DH5d (pCRW2-1; SEQ ID NO: 3) Accession No. NRRL B-21231
2. HB11 DH5d (pCRW5-1; SEQ ID. NO: 47) Accession No. NRRL B-21232
3. *E. coli* DH5d (PCRSTRIT1; SEQ ID NO: 1) Accession No. NRRL B-21233
4. *E. coli* DH5d (pCRR1-21; SEQ ID NO: 4) Accession No. NRRL B-21234
5. *E. coli* DH5d (pCRSNOD31; SEQ ID NO: 2) Accession No. NRRL B-21235

What is claimed is:

1. An isolated Internal Transcribed Spacer sequence selected from the group consisting of: ITS1 of *Septoria tritici*, ITS2 of *Septoria tritici*, ITS1 of *Septoria nodorum*, ITS2 of *Septoria nodorum*, ITS1 of *Pseudocercosporella herpotrichoides* strain W, ITS2 of *Pseudocercosporella herpotrichoides* strain W, ITS1 of *Pseudocercosporella herpotrichoides* strain R, ITS2 of *Pseudocercosporella herpotrichoides* strain R, ITS1 of *Mycosphaerella fijiensis*, ITS2 of *Mycosphaerella fijiensis*, ITS1 of *Mycosphaerella musicola*, and ITS2 of *Mycosphaerella musicola*.

2. An isolated Internal Transcribed Spacer sequence according to claim 1, wherein said Internal Transcribed Spacer sequence is either ITS1 or ITS2 of *Septoria tritici*.

3. A method for the detection of *Septoria tritici*, comprising the steps of:

(a) determining the nucleotide sequence of an Internal Transcribed Spacer sequence according to claim 2;

(b) designing at least one PCR primer having sequence identity with at least 10 consecutive nucleotides of the nucleotide sequence determined in step (a);

(c) isolating DNA from plant tissue infected with *Septoria tritici;*

(d) subjecting said DNA isolated from said plant tissue to polymerase chain reaction amplification using said at least one PCR primer; and (e) detecting *Septoria tritici* by visualizing the product or products of said polymerase chain reaction amplification.

4. An Internal Transcribed Spacer Sequence according to claim 1, wherein said Internal Transcribed Spacer sequence is either ITS1 or ITS2 of *Septoria nodorum*.

5. A method for the detection of *Septoria nodorum*, comprising the steps of:

(a) determining the nucleotide sequence of an Internal Transcribed Spacer sequence according to claim 4;

(b) designing at least one PCR primer having sequence identity with at least 10 consecutive nucleotides of the nucleotide sequence determined in step (a);

(c) isolating DNA from plant tissue infected with *Septoria nodorum;*

(d) subjecting said DNA isolated from said plant tissue to polymerase chain reaction amplification using said at least one PCR primer; and (e) detecting *Septoria nodorum* by visualizing the product or products of said polymerase chain reaction amplification.

6. An Internal Transcribed Spacer Sequence according to claim 1, wherein said Internal Transcribed Spacer sequence is either ITS1 or ITS2 of *Pseudocercosporella herpotrichoides* strain W.

7. A method for the detection of *Pseudocercosporella herpotrichoides* strain W, comprising the steps of:

(a) determining the nucleotide sequence of an Internal Transcribed Spacer sequence according to claim 6;

(b) designing at least one PCR primer having sequence identity with at least 10 consecutive nucleotides of the nucleotide sequence determined in step (a);

(c) isolating DNA from plant tissue infected with *Pseudocercosporella herpotrichoides* strain W;

(d) subjecting said DNA isolated from said plant tissue to polymerase chain reaction amplification using said at least one PCR primer; and (e) detecting *Pseudocercosporella herpotrichoides* strain W by visualizing the product or products of said polymerase chain reaction amplification.

8. An Internal Transcribed Spacer Sequence according to claim 1, wherein said Internal Transcribed Spacer sequence is either ITS1 or ITS2 of *Pseudocercosporella herpotrichoides* strain R.

9. A method for the detection of *Pseudocercosporella herpotrichoides* strain R, comprising the steps of:

(a) determining the nucleotide sequence of an Internal Transcribed Spacer sequence according to claim 8;

(b) designing at least one PCR primer having sequence identity with at least 10 consecutive nucleotides of the nucleotide sequence determined in step (a);

(c) isolating DNA from plant tissue infected with *Pseudocercosporella herpotrichoides* strain R;

(d) subjecting said DNA isolated from said plant tissue to polymerase chain reaction amplification using said at least one PCR primer; and (e) detecting *Pseudocercosporella herpotrichoides* strain R by visualizing the product or products of said polymerase chain reaction amplification.

10. An Internal Transcribed Spacer Sequence according to claim 1, wherein said Internal Transcribed Spacer sequence is either ITS1 or ITS2 of *Mycosphaerella fijiensis*.

11. A method for the detection of *Mycosphaerella fijiensis*, comprising the steps of:

(a) determining the nucleotide sequence of an Internal Transcribed Spacer sequence according to claim 10;

(b) designing at least one PCR primer having sequence identity with at least 10 consecutive nucleotides of the nucleotide sequence determined in step (a);

(c) isolating DNA from plant tissue infected with *Mycosphaerella fijiensis;*

(d) subjecting said DNA isolated from said plant tissue to polymerase chain reaction amplification using said at least one PCR primer; and (e) detecting *Mycosphaerella fijiensis* by visualizing the product or products of said polymerase chain reaction amplification.

12. An Internal Transcribed Spacer Sequence according to claim 1, wherein said Internal Transcribed Spacer sequence is either ITS1 or ITS2 of *Mycosphaerella musicola.*

13. A method for the detection of *Mycosphaerella musicola*, comprising the steps of:

(a) determining the nucleotide sequence of an Internal Transcribed Spacer sequence according to claim 12;

(b) designing at least one PCR primer having sequence identity with at least 10 consecutive nucleotides of the nucleotide sequence determined in step (a);

(c) isolating DNA from plant tissue infected with *Mycosphaerella musicola;*

(d) subjecting said DNA isolated from said plant tissue to polymerase chain reaction amplification using said at least one PCR primer; and (e) detecting *Mycosphaerella musicola* by visualizing the product or products of said polymerase chain reaction amplification.

14. An isolated Internal Transcribed Spacer sequence selected from the group consisting of: nucleotides 31–172 of SEQ ID NO:1, nucleotides 329–490 of SEQ ID NO:1, nucleotides 31–216 of SEQ ID NO:2, nucleotides 373–525 of SEQ ID NO:2, nucleotides 31–262 of SEQ ID NO:3, nucleotides 31–263 of SEQ ID NO:47, nucleotides 419–568 of SEQ ID NO:3, nucleotides 420–569 of SEQ ID NO:47, nucleotides 31–263 of SEQ ID NO:4, nucleotides 420–570 of SEQ ID NO:4, nucleotides 31–171 of SEQ ID NO:5, nucleotides 328–476 of SEQ ID NO:5, nucleotides 31–180 of SEQ ID NO:6, and nucleotides 337–482 of SEQ ID NO:6.

15. An oligonucleotide primer for use in amplification-based detection of a fungal Internal Transcribed Spacer sequence, wherein said primer has sequence identity with at least 10 consecutive nucleotides of a sequence selected from the group consisting of: nucleotides 31–172 of SEQ ID NO:1, nucleotides 329–490 of SEQ ID NO: 1, nucleotides 31–216 of SEQ ID NO:2, nucleotides 373–525 of SEQ ID NO:2, nucleotides 31–262 of SEQ ID NO:3, nucleotides 31–263 of SEQ ID NO:47, nucleotides 419–568 of SEQ ID NO:3, nucleotides 420–569 of SEQ ID NO:47, nucleotides 31–263 of SEQ ID NO:4, nucleotides 420–570 of SEQ ID NO:4, nucleotides 31–108 or 130–171 of SEQ ID NO:5, nucleotides 328–476 of SEQ ID NO:5, nucleotides 31–120 or 139–180 of SEQ ID NO:6, and nucleotides 337–482 of SEQ ID NO:6.

16. A method for the detection of a fungal pathogen, comprising the steps of:

(a) isolating DNA from a plant leaf infected with a pathogen;

(b) subjecting said DNA to polymerase chain reaction amplification using at least one primer according to claim 15; and (c) detecting said fungal pathogen by visualizing the product or products of said polymerase chain reaction amplification.

17. A method according to claim 16, wherein said fungal pathogen is selected from the group consisting of: *Septoria tritici, Septoria nodorum, Pseudocercosporella herpotrichoides* strain W, *Pseudocercosporella herpotrichoides* strain R, *Mycosphaerella fijiensis*, and *Mycosphaerella musicola.*

18. A diagnostic kit used in detecting a fungal pathogen, comprising at least one primer according to claim 15.

19. An oligonucleotide primer according to claim 15, wherein said primer has sequence identity with at least 10 consecutive nucleotides of nucleotides 31–172 of SEQ ID NO:1.

20. A method for the detection of Septoria tritici, comprising the steps of:

(a) isolating DNA from a plant leaf infected with *Septoria tritici;*

(b) subjecting said DNA to polymerase chain reaction amplification using at least one primer according to claim 19; and (c) detecting *Septoria tritici* by visualizing the product or products of said polymerase chain reaction amplification.

21. An oligonucleotide primer according to claim 15, wherein said primer has sequence identity with at least 10 consecutive nucleotides of nucleotides 329–490 of SEQ ID NO: 1.

22. A method for the detection of *Septoria tritici*, comprising the steps of:

(a) isolating DNA from a plant leaf infected with *Septoria tritici;*

(b) subjecting said DNA to polymerase chain reaction amplification using at least one primer according to claim 21; and (c) detecting *Septoria tritici* by visualizing the product or products of said polymerase chain reaction amplification.

23. An oligonucleotide primer according to claim 15, wherein said primer has sequence identity with at least 10 consecutive nucleotides of nucleotides 31–216 of SEQ ID NO:2.

24. A method for the detection of *Septoria nodorum*, comprising the steps of:

(a) isolating DNA from a plant leaf infected with *Septoria nodorum;*

(b) subjecting said DNA to polymerase chain reaction amplification using at least one primer according to claim 23; and (c) detecting *Septoria nodorum* by visualizing the product or products of said polymerase chain reaction amplification.

25. An oligonucleotide primer according to claim 15, wherein said primer has sequence identity with at least 10 consecutive nucleotides of nucleotides 373–525 of SEQ ID NO:2.

26. A method for the detection of *Septoria nodorum*, comprising the steps of:

(a) isolating DNA from a plant leaf infected with *Septoria nodorum;*

(b) subjecting said DNA to polymerase chain reaction amplification using at least one primer according to claim 25; and (c) detecting *Septoria nodorum* by visualizing the product or products of said polymerase chain reaction amplification.

27. An oligonucleotide primer according to claim 15, wherein said primer has sequence identity with at least 10 consecutive nucleotides of nucleotides 31–262 of SEQ ID NO:3 or nucleotides 31–263 of SEQ ID NO:47.

28. A method for the detection of *Pseudocercosporella herpotrichoides* strain W, comprising the steps of:

(a) isolating DNA from a plant leaf infected with *Pseudocercosporella herpotrichoides* strain W;

(b) subjecting said DNA to polymerase chain reaction amplification using at least one primer according to claim 27; and (c) detecting *Pseudocercosporella herpotrichoides* strain W by visualizing the product or products of said polymerase chain reaction amplification.

29. An oligonucleotide primer according to claim 15, wherein said primer has sequence identity with at least 10 consecutive nucleotides of nucleotides 419–568 of SEQ ID NO:3 or nucleotides 420–569 of SEQ ID NO:47.

30. A method for the detection of *Pseudocercosporella herpotrichoides* strain W, comprising the steps of:

(a) isolating DNA from a plant leaf infected with *Pseudocercosporella herpotrichoides* strain W;

(b) subjecting said DNA to polymerase chain reaction amplification using at least one primer according to claim 29; and (c) detecting *Pseudocercosporella herpotrichoides* strain W by visualizing the product or products of said polymerase chain reaction amplification.

31. An oligonucleotide primer according to claim 15, wherein said primer has sequence identity with at least 10 consecutive nucleotides of nucleotides 31–263 of SEQ ID NO:4.

32. A method for the detection of *Pseudocercosporella herpotrichoides* strain R, comprising the steps of:

(a) isolating DNA from a plant leaf infected with *Pseudocercosporella herpotrichoides* strain R;

(b) subjecting said DNA to polymerase chain reaction amplification using at least one primer according to claim 31; and (c) detecting *Pseudocercosporella herpotrichoides* strain R by visualizing the product or products of said polymerase chain reaction amplification.

33. An oligonucleotide primer according to claim 15, wherein said primer has sequence identity with at least 10 consecutive nucleotides of nucleotides 420–570 of SEQ ID NO:4.

34. A method for the detection of *Pseudocercosporella herpotrichoides* strain R, comprising the steps of:

(a) isolating DNA from a plant leaf infected with *Pseudocercosporella herpotrichoides* strain R;

(b) subjecting said DNA to polymerase chain reaction amplification using at least one primer according to claim 33; and (c) detecting *Pseudocercosporella herpotrichoides* strain R by visualizing the product or products of said polymerase chain reaction amplification.

35. An oligonucleotide primer according to claim 15, wherein said primer has sequence identity with at least 10 consecutive nucleotides of nucleotides 31–108 or 130–171 of SEQ ID NO:5.

36. A method for the detection of *Mycosphaerella fijiensis*, comprising the steps of:

(a) isolating DNA from a plant leaf infected with *Mycosphaerella fijiensis;*

(b) subjecting said DNA to polymerase chain reaction amplification using at least one primer according to claim 35; and (c) detecting *Mycosphaerella fijiensis* by visualizing the product or products of said polymerase chain reaction amplification.

37. An oligonucleotide primer according to claim 15, wherein said primer has sequence identity with at least 10 consecutive nucleotides of nucleotides 328–476 of SEQ ID NO:5.

38. A method for the detection of *Mycosphaerella fijiensis*, comprising the steps of:

(a) isolating DNA from a plant leaf infected with a pathogen;

(b) subjecting said DNA to polymerase chain reaction amplification using at least one primer according to claim 37; and (c) detecting *Mycosphaerella fijiensis* by visualizing the product or products of said polymerase chain reaction amplification.

39. An oligonucleotide primer according to claim 15, wherein said primer has sequence identity with at least 10 consecutive nucleotides of nucleotides 31–120 or 139–180 of SEQ ID NO:6.

40. A method for the detection of *Mycosphaerella musicola*, comprising the steps of:

(a) isolating DNA from a plant leaf infected with *Mycosphaerella musicola;*

(b) subjecting said DNA to polymerase chain reaction amplification using at least one primer according to claim 39; and (c) detecting *Mycosphaerella musicola* by visualizing the product or products of said polymerase chain reaction amplification.

41. An oligonucleotide primer according to claim 15, wherein said primer has sequence identity with at least 10 consecutive nucleotides of nucleotides 337–482 of SEQ ID NO:6.

42. A method for the detection of *Mycosphaerella musicola*, comprising the steps of:

(a) isolating DNA from a plant leaf infected with *Mycosphaerella musicola;*

(b) subjecting said DNA to polymerase chain reaction amplification using at least one primer according to claim 41; and (c) detecting *Mycosphaerella musicola* by visualizing the product or products of said polymerase chain reaction amplification.

* * * * *

SEQUENCE LISTING (1) GENERAL INFORMATION:

(iii) NUMBER OF SEQUENCES: 86

(2) INFORMATION FOR SEQ ID NO:1:

(i) SEQUENCE CHARACTERISTICS:
(A) LENGTH: 548 base pairs
(B) TYPE: nucleic acid
(C) STRANDEDNESS: single
(D) TOPOLOGY: linear -continued (ii) MOLECULE TYPE: DNA (genomic)

(iii) HYPOTHETICAL: NO (iv) ANTI-SENSE: NO (ix) FEATURE:
(A) NAME/KEY: misc_feature
(B) LOCATION: 1..548
(D) OTHER INFORMATION: /note= "DNA sequence for the Internal Transcribed Spacer of Septoria tritici"

(xi) SEQUENCE DESCRIPTION: SEQ ID NO:1:

```
TCCGTAGGTG AACCTGCGGA GGGATCATTA CCGAGCGAGG GCCTCCGGGT CCGACCTCCA     60

ACCCTTTGTG AACACATCCC GTTGCTTCGG GGGCGACCCT GCCGGGCGCC CCCGGAGGAC    120

CACCAAAAAA CACTGCATCT CTGCGTCGGA GTTTACGAGT AAATCGAAAC AAAACTTTCA    180

ACAACGGATC TCTTGGTTCT GGCATCGATG AAGAACGCAG CGAAATGCGA TAAGTAATGT    240

GAATTGCAGA ATTCAGTGAA TCATCGAATC TTTGAACGCA CATTGCGCCC CCTGGTATTC    300

CGGGGGGCAT GCCCGTTCGA GCGTCATTAC ACCACTCCAG CCTCGCTGGG TATTGGGCGT    360

CTTTTCGCGG GGGATCACTC CCCCGCGCGC CTCAAAGTCT CCGGCTGAGC GGTCTCGTCT    420

CCCAGCGTTG TGGCATCACG TCTCGCCGCG GAGTTCACGA GCCCTCACGG CCGTTAAATC    480

ACACCTCAGG TTGACCTCGG ATCGGGTAGG GATACCCGCT GAACTTAAGC ATATCAATAA    540

GCGGAGGA                                                             548
```

(2) INFORMATION FOR SEQ ID NO:2:

(i) SEQUENCE CHARACTERISTICS:
(A) LENGTH: 583 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Septoria nodorum (ix) FEATURE:
(A) NAME/KEY: misc_feature
(B) LOCATION: 1..583
(D) OTHER INFORMATION: /note= "DNA sequence for the Internal Transcribed Spacer of Septoria nodorum"

(xi) SEQUENCE DESCRIPTION: SEQ ID NO:2:

```
TCCGTAGGTG AACCTGCGGA AGGATCATTA CACTCAGTAG TTTACTACTG TAAAAGGGGC     60

TGTTAGTCTG TATAGCGCAA GCTGATGAGC AGCTGGCCTC TTTTATCCAC CCTTGTCTTT    120

TGCGTACCCA CGTTTCCTCG GCAGGCTTGC CTGCCGGTTG GACAAATTTA TAACCTTTTT    180

AATTTTCAAT CAGCGTCTGA AAAACTTAAT AATTACAACT TTCAACAACG GATCTCTTGG    240

TTCTGGCATC GATGAAGAAC GCAGCGAAAT GCGATAAGTA GTGTGAATTG CAGAATTCAG    300

TGAATCATCG AATCTTTGAA CGCACATTGC GCCCCTTGGT ATTCCATGGG GCATGCCTGT    360

TCGAGCGTCA TTTGTACCCT CAAGCTCTGC TTGGTGTTGG GTGTTTGTCC TCTCCCTAGT    420

GTTTGGACTC GCCTTAAAAT AATTGGCAGC CAGTGTTTTG GTATTGAAGC GCAGCACAAG    480

TCGCGATTCG TAACAAACAC TTGCGTCCAC AAGCCTTTTT AACTTTTGAC CTCGGATCAG    540

GTAGGGATAC CCGCTGAACT TAAGCATATC AATAAGCGGA GGA                      583
```

-continued (2) INFORMATION FOR SEQ ID NO:3:

(i) SEQUENCE CHARACTERISTICS:
(A) LENGTH: 626 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Pseudocercosporella herpotrichoides
(B) STRAIN: Strain R
(C) INDIVIDUAL ISOLATE: Variant W2-1

(ix) FEATURE:
(A) NAME/KEY: misc_feature
(B) LOCATION: 1..626
(D) OTHER INFORMATION: /note= "DNA sequence for the Internal Transcribed Spacer of Pseudocercosporella herpotrichoides strain W (variant W2-1)"

(xi) SEQUENCE DESCRIPTION: SEQ ID NO:3:

```
TCCGTAGGTG AACCTGCGGA AGGATCATTA ATAGAGCAAT GAACAGACAG CGCCCCGGGA     60

GAAATCCTGG GGGCTACCCT ACTTGGTAGG GTTTAGAGTC GTCAGGCCGC TCGGAGAAGC    120

CTGGTTCAGA CCTCCACCCT TGAATAAATT ACCTTTGTTG CTTTGGCAGG GCGCCTCGCG    180

CCAGCGGCTT CGGCTGTTGA GTACCTGCCA GAGGACCACA ACTCTTGTTT TTAGTGATGT    240

CTGAGTACTA TATAATAGTT AAAACTTTCA ACAACGGATC TCTTGGTTCT GGCATCGATG    300

AAGAACGCAG CGAAATGCGA TAAGTAATGT GAATTGCAGA ATTCAGTGAA TCATCGAATC    360

TTTGAACGCA CATTGCGCCC TCTGGTATTC CGGGGGGCAT GCCTGTTCGA GCGTCATTAT    420

AACCACTCAA GCTCTCGCTT GGTATTGGGG TTCGCGTCCT CGCGGCCTCT AAAATCAGTG    480

GCGGTGCCTG TCGGCTCTAC GCGTAGTAAT ACTCCTCGCG ATTGAGTCCG GTAGGTTTAC    540

TTGCCAGTAA CCCCCAATTT TTTACAGGTT GACCTCGGAT CAGGTAGGGA TACCCGCTGA    600

ACTTAAGCAT ATCAATAAGC GGAGGA                                         626
```

(2) INFORMATION FOR SEQ ID NO:4:

(i) SEQUENCE CHARACTERISTICS:
(A) LENGTH: 627 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Pseudocercosporella herpotrichoides
(B) STRAIN: Strain R (ix) FEATURE:
(A) NAME/KEY: misc_feature
(B) LOCATION: 1..627
(D) OTHER INFORMATION: /note= "DNA sequence for the Internal Transcribed Spacer of Pseudocercosporella herpotrichoides Strain R"

(xi) SEQUENCE DESCRIPTION: SEQ ID NO:4:

```
TCCGTAGGTG AACCTGCGGA AGGATCATTA ATAGAGCAAT GGATAGACAG CGCCCCGGGA     60
```

-continued

```
GAAATCCTGG GGGCCACCCT ACTTCGGTAA GGTTTAGAGT CGTCGGGCCT CTCGGAGAAG    120

CCTGGTCCAG ACCTCCACCC TTGAATAAAT TACCTTTGTT GCTTTGGCAG GGCGCCTCGC    180

GCCAGCGGCT TCGGCTGTTG AGTACCTGCC AGAGGACCAC AACTCTTGTT TTTAGTGATG    240

TCTGAGTACT ATATAATAGT TAAAACTTTC AACAACGGAT CTCTTGGTTC TGGCATCGAT    300

GAAGAACGCA GCGAAATGCG ATAAGTAATG TGAATTGCAG AATTCAGTGA ATCATCGAAT    360

CTTTGAACGC ACATTGCGCC CTCTGGTATT CCGGGGGGCA TGCCTGTTCG AGCGTCATTA    420

TAACCACTCA AGCTCTCGCT TGGTATTGGG GTTCGCGTCT TCGCGGCCTC TAAAATCAGT    480

GGCGGTGCCT GTCGGCTCTA CGCGTAGTAA TACTCCTCGC GATTGAGTCC GGTAGGTTTA    540

CTTGCCAGCA ACCCCCAATT TTTTACAGGT TGACCTCGGA TCAGGTAGGG ATACCCGCTG    600

AACTTAAGCA TATCAATAAG CGGAGGA                                        627
```

(2) INFORMATION FOR SEQ ID NO:5:

(i) SEQUENCE CHARACTERISTICS:
(A) LENGTH: 534 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Mycosphaerella fijiensis (ix) FEATURE:
(A) NAME/KEY: misc_feature
(B) LOCATION: 1..534
(D) OTHER INFORMATION: /note= "DNA sequence for the Internal Transcribed Spacer of Mycosphaerella fijiensis"

(xi) SEQUENCE DESCRIPTION: SEQ ID NO:5:

```
TCCGTAGGTG AACCTGCGGA GGGATCATTA CCGAGTGAGG GCTCACGCCC GACCTCCAAC     60

CCTTTGTGAA CCACAACTTG TTGCTTCGGG GGCGACCTGC CGTCGGCGGG CGCCCCCGGA    120

GGCCGTCTAA ACACTGCATC TTTGCGTCGG AGTTTAAAAC AAATCGAACA AAACTTTCAA    180

CAACGGATCT CTTGGTTCTG GCATCGATGA AGAACGCAGC GAAATGCGAT AAGTAATGTG    240

AATTGCAGAA TTCAGTGAAT CATCGAATCT TTGAACGCAC ATTGCGCCCT TTGGTATTCC    300

GAAGGGCATG CCTGTTCGAG CGTCATTTCA CCACTCAAGC CTGGCTTGGT ATTGGGCGTC    360

GCGGTTCTTC GCGCGCCTTA AAGTCTCCGG CTGAGCTGTC CGTCTCTAAG CGTTGTGGAT    420

CTTTCAATTC GCTTCGGAGT GCGGGTGGCC GCGGCCGTTA AATCTTTATT CAAAGGTTGA    480

CCTCGGATCA GGTAGGGATA CCCGCTGAAC TTAAGCATAT CAATAAGCGG AGGA          534
```

(2) INFORMATION FOR SEQ ID NO:6:

(i) SEQUENCE CHARACTERISTICS:
(A) LENGTH: 540 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Mycosphaerella musicola (ix) FEATURE:
(A) NAME/KEY: misc_feature
(B) LOCATION: 1..540
(D) OTHER INFORMATION: /note= "DNA sequence for the Internal Transcribed Spacer of Mycosphaerella musicola"

(xi) SEQUENCE DESCRIPTION: SEQ ID NO:6:

TCCGTAGGTG AACCTGCGGG GGGATCATTA CCGAGTGAGG GCTCACCCCC GACCTCCAAC 60

CCTTTGTGAA CCACACCTGT TGCTTCGGGG GCGACCCTGC CGGCGAACTT GTCGCCGGGC 120

GCCCCCGGAG GTCTCCTTAA CACTGCATCT CTGCGTCGGA GTTCCAAACA AATCGGACAA 180

AACTTTCAAC AACGGATCTC TTGGTTCTGG CATCGATGAA GAACGCAGCG AAATGCGATA 240

AGTAATGTGA ATTGCAGAAT TCAGTGAATC ATCGAATCTT TGAACGCACA TTGCGCCCTT 300

TGGCATTCCG AAGGGCATGC CTGTTCGAGC GTCATTTCAC CACTCAAGCC TAGCTTGGTA 360

TTGGGCGCCG CGGTGCTCCG CGCGCCCCAA AGTCTCCCGG CTAAGCCGTC CGTCTCTAAG 420

CGTTGTGGAT TTTTCAGTTC GCTCCGGAGC GCGGGTGGCC GCGGCCGTTA AATCTTCAAA 480

GGTTGACCTC GGATCAGGTA GGGATACCCG CTGAACTTAA GCATATCAAT AAGCGGAGGA 540

(2) INFORMATION FOR SEQ ID NO:7:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB433

(iii) HYPOTHETICAL: NO (iv) ANTI-SENSE: NO (xi) SEQUENCE DESCRIPTION: SEQ ID NO:7:

ACACTCAGTA GTTTACTACT 20

(2) INFORMATION FOR SEQ ID NO:8:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB434

(iii) HYPOTHETICAL: NO (iv) ANTI-SENSE: NO (xi) SEQUENCE DESCRIPTION: SEQ ID NO:8:

TGTGCTGCGC TTCAATA 17

(2) INFORMATION FOR SEQ ID NO:9:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB525

(iii) HYPOTHETICAL: NO (iv) ANTI-SENSE: NO (xi) SEQUENCE DESCRIPTION: SEQ ID NO:9:

GCGACTTGTG CTGCGCTTCA ATA 23

(2) INFORMATION FOR SEQ ID NO:10:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB527

(iii) HYPOTHETICAL: NO (iv) ANTI-SENSE: NO (xi) SEQUENCE DESCRIPTION: SEQ ID NO:10:

CATTACACTC AGTAGTTTAC TACT 24

(2) INFORMATION FOR SEQ ID NO:11:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB445

(iii) HYPOTHETICAL: NO (iv) ANTI-SENSE: NO (xi) SEQUENCE DESCRIPTION: SEQ ID NO:11:

CTGCGTCGGA GTTTACG 17

(2) INFORMATION FOR SEQ ID NO:12:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB446

(iii) HYPOTHETICAL: NO (iv) ANTI-SENSE: NO (xi) SEQUENCE DESCRIPTION: SEQ ID NO:12:

CGAGGCTGGA GTGGTGT 17

(2) INFORMATION FOR SEQ ID NO:13:

(i) SEQUENCE CHARACTERISTICS:
(A) LENGTH: 22 base pairs
(B) TYPE: nucleic acid
(C) STRANDEDNESS: single
(D) TOPOLOGY: linear -continued (ii) MOLECULE TYPE: Other nucleic acid
(A) DESCRIPTION: Oligonucleotide primer JB526

(iii) HYPOTHETICAL: NO (iv) ANTI-SENSE: NO (xi) SEQUENCE DESCRIPTION: SEQ ID NO:13:

CCCAGCGAGG CTGGAGTGGT GT 22

(2) INFORMATION FOR SEQ ID NO:14:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB536

(iii) HYPOTHETICAL: NO (iv) ANTI-SENSE: NO (xi) SEQUENCE DESCRIPTION: SEQ ID NO:14:

CTGGGGGCTA CCCTACTTGG TAG 23

(2) INFORMATION FOR SEQ ID NO:15:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB537

(iii) HYPOTHETICAL: NO (iv) ANTI-SENSE: NO (xi) SEQUENCE DESCRIPTION: SEQ ID NO:15:

GGGGGCTACC CTACTTGGTA G 21

(2) INFORMATION FOR SEQ ID NO:16:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB538

(iii) HYPOTHETICAL: NO (iv) ANTI-SENSE: NO (xi) SEQUENCE DESCRIPTION: SEQ ID NO:16:

ACTTGGTAGG GTTTAGAGTC GTCA 24

(2) INFORMATION FOR SEQ ID NO:17:

(i) SEQUENCE CHARACTERISTICS:
(A) LENGTH: 24 base pairs
(B) TYPE: nucleic acid
(C) STRANDEDNESS: single
(D) TOPOLOGY: linear -continued (ii) MOLECULE TYPE: Other nucleic acid
(A) DESCRIPTION: Oligonucleotide primer JB539

(iii) HYPOTHETICAL: NO (iv) ANTI-SENSE: NO (xi) SEQUENCE DESCRIPTION: SEQ ID NO:17:

CTTCGGTAAG GTTTAGAGTC GTCG 24

(2) INFORMATION FOR SEQ ID NO:18:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB540

(iii) HYPOTHETICAL: NO (iv) ANTI-SENSE: NO (xi) SEQUENCE DESCRIPTION: SEQ ID NO:18:

GGGGGCCACC CTACTTCGGT AA 22

(2) INFORMATION FOR SEQ ID NO:19:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB541

(iii) HYPOTHETICAL: NO (iv) ANTI-SENSE: NO (xi) SEQUENCE DESCRIPTION: SEQ ID NO:19:

CCACTGATTT TAGAGGCCGC GAG 23

(2) INFORMATION FOR SEQ ID NO:20:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB542

(iii) HYPOTHETICAL: NO (iv) ANTI-SENSE: NO (xi) SEQUENCE DESCRIPTION: SEQ ID NO:20:

CCACTGATTT TAGAGGCCGC GAA 23

(2) INFORMATION FOR SEQ ID NO:21:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB543

(iii) HYPOTHETICAL: NO (iv) ANTI-SENSE: NO (xi) SEQUENCE DESCRIPTION: SEQ ID NO:21:

CCTGTAAAAA ATTGGGGGTT A 21

(2) INFORMATION FOR SEQ ID NO:22:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB544

(iii) HYPOTHETICAL: NO (iv) ANTI-SENSE: NO (xi) SEQUENCE DESCRIPTION: SEQ ID NO:22:

CCTGTAAAAA ATTGGGGGTT G 21

(2) INFORMATION FOR SEQ ID NO:23:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB547

(iii) HYPOTHETICAL: NO (iv) ANTI-SENSE: NO (xi) SEQUENCE DESCRIPTION: SEQ ID NO:23:

ATTACCGAGT GAGGGCTCAC GC 22

(2) INFORMATION FOR SEQ ID NO:24:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB548

(iii) HYPOTHETICAL: NO (iv) ANTI-SENSE: NO (xi) SEQUENCE DESCRIPTION: SEQ ID NO:24:

GTTGCTTCGG GGGCGACCTG 20

(2) INFORMATION FOR SEQ ID NO:25:

(i) SEQUENCE CHARACTERISTICS:
(A) LENGTH: 17 base pairs
(B) TYPE: nucleic acid
(C) STRANDEDNESS: single
(D) TOPOLOGY: linear -continued (ii) MOLECULE TYPE: Other nucleic acid
(A) DESCRIPTION: Oligonucleotide primer JB442

(iii) HYPOTHETICAL: NO (iv) ANTI-SENSE: NO (xi) SEQUENCE DESCRIPTION: SEQ ID NO:25:

TCGGGGGCGA CCTGCCG 17

(2) INFORMATION FOR SEQ ID NO:26:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB443

(iii) HYPOTHETICAL: NO (iv) ANTI-SENSE: NO (xi) SEQUENCE DESCRIPTION: SEQ ID NO:26:

CCGGAGGCCG TCTA 14

(2) INFORMATION FOR SEQ ID NO:27:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB545

(iii) HYPOTHETICAL: NO (iv) ANTI-SENSE: NO (xi) SEQUENCE DESCRIPTION: SEQ ID NO:27:

CCACAACGCT TAGAGACGGA CAG 23

(2) INFORMATION FOR SEQ ID NO:28:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB546

(iii) HYPOTHETICAL: NO (iv) ANTI-SENSE: NO (xi) SEQUENCE DESCRIPTION: SEQ ID NO:28:

CACCCGCACT CCGAAGCGAA TT 22

(2) INFORMATION FOR SEQ ID NO:29:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB549

(iii) HYPOTHETICAL: NO (iv) ANTI-SENSE: NO (xi) SEQUENCE DESCRIPTION: SEQ ID NO:29:

GATCCGAGGT CAACCTTTGA ATAA 24

(2) INFORMATION FOR SEQ ID NO:30:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB444

(iii) HYPOTHETICAL: NO (iv) ANTI-SENSE: NO (xi) SEQUENCE DESCRIPTION: SEQ ID NO:30:

GGTCAACCTT TGAATAA 17

(2) INFORMATION FOR SEQ ID NO:31:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB451

(iii) HYPOTHETICAL: NO (iv) ANTI-SENSE: NO (xi) SEQUENCE DESCRIPTION: SEQ ID NO:31:

CCTTTGTGAA CCACACCT 18

(2) INFORMATION FOR SEQ ID NO:32:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB440

(iii) HYPOTHETICAL: NO (iv) ANTI-SENSE: NO (xi) SEQUENCE DESCRIPTION: SEQ ID NO:32:

CTGCCGGCGA ACTT 14

(2) INFORMATION FOR SEQ ID NO:33:

(i) SEQUENCE CHARACTERISTICS:
(A) LENGTH: 17 base pairs
(B) TYPE: nucleic acid
(C) STRANDEDNESS: single
(D) TOPOLOGY: linear -continued (ii) MOLECULE TYPE: Other nucleic acid
(A) DESCRIPTION: Oligonucleotide primer JB449

(iii) HYPOTHETICAL: NO (iv) ANTI-SENSE: NO (xi) SEQUENCE DESCRIPTION: SEQ ID NO:33:

ACCCTGCCGG CGAACTT 17

(2) INFORMATION FOR SEQ ID NO:34:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB448

(iii) HYPOTHETICAL: NO (iv) ANTI-SENSE: NO (xi) SEQUENCE DESCRIPTION: SEQ ID NO:34:

GCGACCCTGC CGGCGAAC 18

(2) INFORMATION FOR SEQ ID NO:35:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB441

(iii) HYPOTHETICAL: NO (iv) ANTI-SENSE: NO (xi) SEQUENCE DESCRIPTION: SEQ ID NO:35:

TAGCCGGGAG ACTTTGG 17

(2) INFORMATION FOR SEQ ID NO:36:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer JB450

(iii) HYPOTHETICAL: NO (iv) ANTI-SENSE: NO (xi) SEQUENCE DESCRIPTION: SEQ ID NO:36:

TCTGCGTCGG AGTTCC 16

(2) INFORMATION FOR SEQ ID NO:37:

(i) SEQUENCE CHARACTERISTICS:
(A) LENGTH: 18 base pairs
(B) TYPE: nucleic acid
(C) STRANDEDNESS: single
(D) TOPOLOGY: linear -continued (ii) MOLECULE TYPE: Other nucleic acid
(A) DESCRIPTION: Oligonucleotide primer JB452

(iii) HYPOTHETICAL: NO (iv) ANTI-SENSE: NO (xi) SEQUENCE DESCRIPTION: SEQ ID NO:37:

CCGCGCTCCG GAGCGAAC 18

(2) INFORMATION FOR SEQ ID NO:38:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer ITS1

(iii) HYPOTHETICAL: NO (iv) ANTI-SENSE: NO (xi) SEQUENCE DESCRIPTION: SEQ ID NO:38:

TCCGTAGGTG AACCTGCGG 19

(2) INFORMATION FOR SEQ ID NO:39:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer ITS2

(iii) HYPOTHETICAL: NO (iv) ANTI-SENSE: NO (xi) SEQUENCE DESCRIPTION: SEQ ID NO:39:

GCTGCGTTCT TCATCGATGC 20

(2) INFORMATION FOR SEQ ID NO:40:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer ITS3

(iii) HYPOTHETICAL: NO (iv) ANTI-SENSE: NO (xi) SEQUENCE DESCRIPTION: SEQ ID NO:40:

GCATCGATGA AGAACGCAGC 20

(2) INFORMATION FOR SEQ ID NO:41:

(i) SEQUENCE CHARACTERISTICS:
(A) LENGTH: 20 base pairs
(B) TYPE: nucleic acid
(C) STRANDEDNESS: single
(D) TOPOLOGY: linear -continued (ii) MOLECULE TYPE: Other nucleic acid
(A) DESCRIPTION: Oligonucleotide primer ITS4

(iii) HYPOTHETICAL: NO (iv) ANTI-SENSE: NO (xi) SEQUENCE DESCRIPTION: SEQ ID NO:41:

TCCTCCGCTT ATTGATATGC 20

(2) INFORMATION FOR SEQ ID NO:42:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer OPB-12

(iii) HYPOTHETICAL: NO (iv) ANTI-SENSE: NO (xi) SEQUENCE DESCRIPTION: SEQ ID NO:42:

CCTTGACGCA 10

(2) INFORMATION FOR SEQ ID NO:43:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer OPE-6

(iii) HYPOTHETICAL: NO (iv) ANTI-SENSE: NO (xi) SEQUENCE DESCRIPTION: SEQ ID NO:43:

AAGACCCCTC 10

(2) INFORMATION FOR SEQ ID NO:44:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer OPE-12

(iii) HYPOTHETICAL: NO (iv) ANTI-SENSE: NO (xi) SEQUENCE DESCRIPTION: SEQ ID NO:44:

TTATCGCCCC 10

(2) INFORMATION FOR SEQ ID NO:45:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer OPE-19

(iii) HYPOTHETICAL: NO (iv) ANTI-SENSE: NO (xi) SEQUENCE DESCRIPTION: SEQ ID NO:45:

ACCCCCGAAG 10

(2) INFORMATION FOR SEQ ID NO:46:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: Other nucleic acid
(A) DESCRIPTION: Oligonucleotide primer OPE-15

(iii) HYPOTHETICAL: NO (iv) ANTI-SENSE: NO (xi) SEQUENCE DESCRIPTION: SEQ ID NO:46:

ACGCACAACC 10

(2) INFORMATION FOR SEQ ID NO:47:

(i) SEQUENCE CHARACTERISTICS:
(A) LENGTH: 627 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Pseudocercosporella herpotrichoides
(B) STRAIN: Strain W
(C) INDIVIDUAL ISOLATE: Variant W5-1

(ix) FEATURE:
(A) NAME/KEY: misc_feature
(B) LOCATION: 1..627
(D) OTHER INFORMATION: /note= "DNA sequence for the Internal Transcribed Spacer of Pseudocercosporella herpitrichoides strain W (variant W5-1)"

(xi) SEQUENCE DESCRIPTION: SEQ ID NO:47:

TCCGTAGGTG AACCTGCGGA AGGATCATTA ATAGAGCAAT GAACAGACAG CGCCCTGGGA 60

GAAATCCTGG GGGCTACCCT ACTTCGGTAG GGTTTAGAGT CGTCAGGCCT CTCGGAGAAG 120

CCTGGTTCAG ACCTCCACCC TTGAATAAAT TACCTTTGTT GCTTTGGCAG GGCGCCTCGC 180

GCCAGCGGCT TCGGCTGTTG AGTACCTGCC AGAGGACCAC AACTCTTGTT TTTAGTGATG 240

TCTGAGTACT ATATAATAGT TAAAACTTTC AACAACGGAT CTCTTGGTTC TGGCATCGAT 300

GAAGAACGCA GCGAAATGCG ATAAGTAATG TGAATTGCAG AATTCAGTGA ATCATCGAAT 360

CTTTGAACGC ACATTGCGCC CTCTGGTATT CCGGGGGGCA TGCCTGTTCG AGCGTCATTA 420

TAACCACTCA AGCTCTCGCT TGGTATTGGG GTTCGCGTCC TCGCGGCCTC TAAAATCAGT 480

GGCGGTGCCT CTCGGCTCTA CGCGTAGTAA TACTCCTCGC GATTGAGTCC GGTAGGTTTA 540

CTTGCCAGTA ACCCCCAATT TTTTACAGGT TGACCTCGGA TCAGGTAGGG ATACCCGCTG 600

-continued

AACTTAAGCA TATCAATAAG CGGAGGA 627

(2) INFORMATION FOR SEQ ID NO:48:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: Other nucleic acid
(A) DESCRIPTION: M13 universal -20 oligonucleotide primer (iii) HYPOTHETICAL: NO (iv) ANTI-SENSE: NO (xi) SEQUENCE DESCRIPTION: SEQ ID NO:48:

GTAAAACGAC GGCCAGT 17

(2) INFORMATION FOR SEQ ID NO:49:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: Other nucleic acid
(A) DESCRIPTION: M13 universal reverse oligonucleotide primer (iii) HYPOTHETICAL: NO (iv) ANTI-SENSE: NO (xi) SEQUENCE DESCRIPTION: SEQ ID NO:49:

AACAGCTATG ACCATG 16

(2) INFORMATION FOR SEQ ID NO:50:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB563"

(iii) HYPOTHETICAL: NO (xi) SEQUENCE DESCRIPTION: SEQ ID NO:50:

CTTGCCTGCC GGTTGGACAA ATT 23

(2) INFORMATION FOR SEQ ID NO:51:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide JB564"

(iii) HYPOTHETICAL: NO (xi) SEQUENCE DESCRIPTION: SEQ ID NO:51:

CTCAGTAGTT TACTACTGTA AAAGG 25

(2) INFORMATION FOR SEQ ID NO:52:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide JB565"

(iii) HYPOTHETICAL: NO (xi) SEQUENCE DESCRIPTION: SEQ ID NO:52:

CTTCTGGACG CAAGTGTTTG TTAC 24

(2) INFORMATION FOR SEQ ID NO:53:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide JB566"

(iii) HYPOTHETICAL: NO (xi) SEQUENCE DESCRIPTION: SEQ ID NO:53:

GTTTTTAGTG GAACTTCTGA GT 22

(2) INFORMATION FOR SEQ ID NO:54:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide JB567"

(iii) HYPOTHETICAL: NO (xi) SEQUENCE DESCRIPTION: SEQ ID NO:54:

CGCAGGAACC CTAAACTCT 19

(2) INFORMATION FOR SEQ ID NO:55:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB568"

(iii) HYPOTHETICAL: NO (xi) SEQUENCE DESCRIPTION: SEQ ID NO:55:

GCCCGCCGCA GG 12

(2) INFORMATION FOR SEQ ID NO:56:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB569"

(iii) HYPOTHETICAL: NO (xi) SEQUENCE DESCRIPTION: SEQ ID NO:56:

RTWWTTWRTG GAMYYTCTGA GT 22

(2) INFORMATION FOR SEQ ID NO:57:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB570"

(iii) HYPOTHETICAL: NO (xi) SEQUENCE DESCRIPTION: SEQ ID NO:57:

TATGTTGCCT CGGCGG 16

(2) INFORMATION FOR SEQ ID NO:58:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB571"

(iii) HYPOTHETICAL: NO (xi) SEQUENCE DESCRIPTION: SEQ ID NO:58:

TAACGATATG TAAATTACTA CGCT 24

(2) INFORMATION FOR SEQ ID NO:59:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB572"

(iii) HYPOTHETICAL: NO (xi) SEQUENCE DESCRIPTION: SEQ ID NO:59:

AAGTTGGGGT TTAACGGC 18

(2) INFORMATION FOR SEQ ID NO:60:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB573"

(iii) HYPOTHETICAL: NO (xi) SEQUENCE DESCRIPTION: SEQ ID NO:60:

AGCGAGCCCG CCAC 14

-continued (2) INFORMATION FOR SEQ ID NO:61:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB574"

(iii) HYPOTHETICAL: NO (xi) SEQUENCE DESCRIPTION: SEQ ID NO:61:

CCATTGTGAA CGTTACCTAT AC 22

(2) INFORMATION FOR SEQ ID NO:62:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB575"

(iii) HYPOTHETICAL: NO (xi) SEQUENCE DESCRIPTION: SEQ ID NO:62:

CGACCAGAGC GAGATGTA 18

(2) INFORMATION FOR SEQ ID NO:63:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB576"

(iii) HYPOTHETICAL: NO (xi) SEQUENCE DESCRIPTION: SEQ ID NO:63:

GTGAACATAC CTTATGTTGC C 21

(2) INFORMATION FOR SEQ ID NO:64:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB577"

(iii) HYPOTHETICAL: NO (xi) SEQUENCE DESCRIPTION: SEQ ID NO:64:

GTTGCCTCGG CGGATC 16

(2) INFORMATION FOR SEQ ID NO:65:

(i) SEQUENCE CHARACTERISTICS:
(A) LENGTH: 16 base pairs
(B) TYPE: nucleic acid
(C) STRANDEDNESS: single (D) TOPOLOGY: linear (ii) MOLECULE TYPE: other nucleic acid
(A) DESCRIPTION: /desc = "Oligonucleotide primer JB578"

(iii) HYPOTHETICAL: NO (xi) SEQUENCE DESCRIPTION: SEQ ID NO:65:

CCGCGACGAT TACCAG 16

(2) INFORMATION FOR SEQ ID NO:66:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB538'"

(iii) HYPOTHETICAL: NO (xi) SEQUENCE DESCRIPTION: SEQ ID NO:66:

TGACGACTCT AAACCCTACC A 21

(2) INFORMATION FOR SEQ ID NO:67:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB539'"

(iii) HYPOTHETICAL: NO (xi) SEQUENCE DESCRIPTION: SEQ ID NO:67:

CGACGACTCT AAACCTTACC G 21

(2) INFORMATION FOR SEQ ID NO:68:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer W130"

(iii) HYPOTHETICAL: NO (xi) SEQUENCE DESCRIPTION: SEQ ID NO:68:

ATTCAAGGGT GGAGGTCTGA 20

(2) INFORMATION FOR SEQ ID NO:69:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer R130"

(iii) HYPOTHETICAL: NO (xi) SEQUENCE DESCRIPTION: SEQ ID NO:69:

ATTCAAGGGT GGAGGTCTGG 20

(2) INFORMATION FOR SEQ ID NO:70:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB539'15"

(iii) HYPOTHETICAL: NO (xi) SEQUENCE DESCRIPTION: SEQ ID NO:70:

CTCTAAACCC TACCA 15

(2) INFORMATION FOR SEQ ID NO:71:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB539'15"

(iii) HYPOTHETICAL: NO (xi) SEQUENCE DESCRIPTION: SEQ ID NO:71:

CTCTAAACCT TACCG 15

(2) INFORMATION FOR SEQ ID NO:72:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB553"

(iii) HYPOTHETICAL: NO (xi) SEQUENCE DESCRIPTION: SEQ ID NO:72:

GTGGTCCTCT GGCAG 15

(2) INFORMATION FOR SEQ ID NO:73:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB554"

(iii) HYPOTHETICAL: NO (xi) SEQUENCE DESCRIPTION: SEQ ID NO:73:

CTCAACAGCC GAAGC 15

(2) INFORMATION FOR SEQ ID NO:74:

(i) SEQUENCE CHARACTERISTICS:
(A) LENGTH: 14 base pairs (B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB555"

(iii) HYPOTHETICAL: NO (xi) SEQUENCE DESCRIPTION: SEQ ID NO:74:

GGGTGGAGGT CTGA 14

(2) INFORMATION FOR SEQ ID NO:75:

(i) SEQUENCE CHARACTERISTICS:
(A) LENGTH: 13 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB556"

(iii) HYPOTHETICAL: NO (xi) SEQUENCE DESCRIPTION: SEQ ID NO:75:

GGTGGAGGTC TGG 13

(2) INFORMATION FOR SEQ ID NO:76:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB561"

(iii) HYPOTHETICAL: NO (xi) SEQUENCE DESCRIPTION: SEQ ID NO:76:

TGGAGGTCTG GACCA 15

(2) INFORMATION FOR SEQ ID NO:77:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB562"

(iii) HYPOTHETICAL: NO (xi) SEQUENCE DESCRIPTION: SEQ ID NO:77:

TGGAGGTCTG AACCA 15

(2) INFORMATION FOR SEQ ID NO:78:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB559"

(iii) HYPOTHETICAL: NO (xi) SEQUENCE DESCRIPTION: SEQ ID NO:78:

AGGGTGGAGG TCTGA 15

(2) INFORMATION FOR SEQ ID NO:79:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB560"

(iii) HYPOTHETICAL: NO (xi) SEQUENCE DESCRIPTION: SEQ ID NO:79:

AGGGTGGAGG TCTGG 15

(2) INFORMATION FOR SEQ ID NO:80:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB557"

(iii) HYPOTHETICAL: NO (xi) SEQUENCE DESCRIPTION: SEQ ID NO:80:

TTCTCCGAGA GGCCT 15

(2) INFORMATION FOR SEQ ID NO:81:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide primer JB558"

(iii) HYPOTHETICAL: NO (xi) SEQUENCE DESCRIPTION: SEQ ID NO:81:

TTCTCCGAGA GGCCC 15

(2) INFORMATION FOR SEQ ID NO:82:

(i) SEQUENCE CHARACTERISTICS:
(A) LENGTH: 504 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (ix) FEATURE:
(A) NAME/KEY: misc_feature
(B) LOCATION: 1..504
(D) OTHER INFORMATION: /note= "DNA sequence for the internal transcribed spacer region of Fusarium culmorum (fculm.con)"

(xi) SEQUENCE DESCRIPTION: SEQ ID NO:82:

-continued

```
GAGGGATCAT TACCGAGTTT ACTRACTCCC AAACCCCTGT GAACDTACCT TATGTTGCCT     60

CGGCGGATCA GCCCGCGCCC CGTAAAAAGG GACGGCCCGC CGCAGGAACC CTAAACTCTG    120

TTTTTAGTGG AACTTCTGAG TATAAAAAAC AAATAAATCA AAACTTTCAA CAACGGATCT    180

CTTGGTTCTG GCATCGATGA AGAACGCAGC AAAATGCGAT AAGTAATGTG AATTGCAGAA    240

TTCAGTGAAT CATCGAATCT TTGAACGCAC ATTGCGCCCG CCAGTATTCT GGCGGGCATG    300

CCTGTTCGAG CGTCATTTCA ACCCTCAAGC CCAGCTTGGT GTTGGGAGCT GCAGTCCTGC    360

TGCACTCCCC AAATACATTG GCGGTCACGT CGRAGCTTCC ATAGCGTAGT AATTTACATA    420

TCGTTACTGG TAATCGTCGC GGCYACGCCG TTAAACCCCA ACTTCTGAAT GTTGACCTCG    480

GATCAGGTAG GAATACCCGC TGAA                                           504
```

(2) INFORMATION FOR SEQ ID NO:83:

(i) SEQUENCE CHARACTERISTICS:
(A) LENGTH: 503 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (ix) FEATURE:
(A) NAME/KEY: misc_feature
(B) LOCATION: 1..503
(D) OTHER INFORMATION: /note= "DNA sequence for the internal transcribed spacer region of Fusarium graminearum (fgram.con)"

(xi) SEQUENCE DESCRIPTION: SEQ ID NO:83:

```
GGATCATTAC CGAGTTTACW SACTCCCAAA CCCCTGTGAA CATACCTTAT GTTGCCTCGG     60

CGGATCAGCC CGCGCCCCGA AAGGGACGGC CCGCCGCAGG AACCCTAAAC TCTGTTTTTA    120

GTGGAACTTC TGAGTATAAA AAACAAATAA ATCAAAACTT TCAACAACGG ATCTCTTGGT    180

KCTGGCATCG ATGAAGAACG CASCRAAATG CGATAAGTAA TGTGWATTGC AGAATTCAGT    240

GAATCAWCGA ATCTTTGAAC GCWSATTGCK MCCRCCAGTA TTCTGGCGGG CATGCCTGTT    300

CGAGCGTCAT TTCAACCCTC AAGCCCAGVT TGGTGTKGGG GARYTGCAGK CCTRYTKCAC    360

TCCCCAAATA ARTTGGCGGT CACGTCGAAC TTCCATAGCG TAGTAAGTTA CACATCGTTA    420

CTGGTAATCG TCGCGGCTAC GCCGTTAAAC CCCAACTTCT GAATGTTGAC CTCGGATCAG    480

GTAGGAATAC CCGCTGAAGG TAA                                            503
```

(2) INFORMATION FOR SEQ ID NO:84:

(i) SEQUENCE CHARACTERISTICS:
(A) LENGTH: 353 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (ix) FEATURE:
(A) NAME/KEY: misc_feature
(B) LOCATION: 1..353
(D) OTHER INFORMATION: /note= "DNA sequence for the internal transcribed spacer region of Fusarium moniliforme (fmono.con)"

(xi) SEQUENCE DESCRIPTION: SEQ ID NO:84:

```
TCCGTAGGTG AACCTGCGGA TAGGRGTCAT TASMGAGTTT ACWACTSCCA AACCCCTGTG     60

AAYATACCTT ATGTTGCSTC GGCGGATCAG CCCGCGCSCC GTARRAAGGG ACGGCCCGCC    120

GCAGGAACCC TAAACTCTGT TTTTAGTGGA ACTTCTGAGT ATAAAAAACA AATAAATCAA    180

AACTTTCAAC AACGGATCTC TTGGTTCTGG CATCGATGAA GAACGCAGCA AAATGCGATA    240

AGTAATGTGA ATTGCAGAAT TCAGTGAATC ATCGAATCTT TGAACGCACA TTGYGMCCGC    300

CAGTATTCTG GCGGGCATGC CTGTTCGAGC GTCATTTCAA CCCTCAAGCC CAG           353
```

(2) INFORMATION FOR SEQ ID NO:85:

(i) SEQUENCE CHARACTERISTICS:
(A) LENGTH: 545 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (ix) FEATURE:
(A) NAME/KEY: misc_feature
(B) LOCATION: 1..545
(D) OTHER INFORMATION: /note= "DNA sequence for the internal transcribed spacer region of Microdochium nivale (mnivale.txt)"

(xi) SEQUENCE DESCRIPTION: SEQ ID NO:85:

```
GCGGATCATT ACAGAGTTGC AAAACTCCCT AAACCATTGT GAACGTTACC TATACCGTTG     60

CTTCGGCGGG CGGCCCCGGG GTTTACCCCC CGGRAGYCCC TGGKMCCCAC CGCGGGSGCC    120

MGCCGGAGGT CACCAAACTC TTGATAATTT ATGGCCTCTC TGAGTCTTCT GTACTGAATA    180

AGTCAAAACT TTCAACAACG GATCTCTTGG TTCTGGCATC GATGAAGAAC GCAGCGAAAT    240

GCGATAAGTA ATGTGAATTG CAGAATTCAG TGAATCATCG AATCTTTGAA CGCACATTGC    300

GCCCGCCAGC ATTCTGGCGG GCATGCCTGT TCGAGCGTCA TTTCAACCAT CAAGCCCCCG    360

GGCTTGTGTT GGGGACCTRC GGCTGCCGCA GGCCCTGAAA AGCAGTGKCG GGCTCGCTGT    420

CGCACCGAGM GTAGTAGSAT ACATCTCGCT CTGGTCGCGC CGCGGGTTCC GGCCGTTAAA    480

CCACCTTTTT AACCCAAGGT TGACCTCGGA TCAGGTAGGA AGACCCGCTG AACTTACGCA    540

TATCA                                                                545
```

(2) INFORMATION FOR SEQ ID NO:86:

(i) SEQUENCE CHARACTERISTICS:
(A) LENGTH: 563 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (ix) FEATURE:
(A) NAME/KEY: misc_feature
(B) LOCATION: 1..563
(D) OTHER INFORMATION: /note= "DNA sequence for the internal transcribed spacer of Septoria avenae f. sp. tricicea ATCC# 26380 (satits.con)"

(xi) SEQUENCE DESCRIPTION: SEQ ID NO:86:

```
TCCCGTAGGT GAACCTGCGG AAGGATCATT ACACTCAGTA GTTTACTACT GTAAAGGAGG     60

CTGTTAGTCT GTATAGCGCA AGCTGATGAG CAGCTAGCCT CTTTTATCCA CCCTTGTCTT    120
```

-continued

```
TTGCGTACCC ACGTTTCCTC GGCAGGCTTG CCTGCCGATT GGACAAACCT ATAACCTTTT    180

TAATTTTCAA TCAGCGTCTG AAAAACTTAA TAATTACAAC TTTCAACAAC GGATCTCTTG    240

GTTCTGGCAT CGATGAAGAA CGCAGCGAAA TGCGATAAGT AGTGTGAATT GCAGAATTCA    300

GTGAATCATC GAATCTTTGA ACGCACATTG CGCCCCTTGG TATTCCATGG GGCATGCCTG    360

TTCGAGCGTC ATTTGTACCC TCAAGCTCTG CTTGGTGTTG GGTGTTTGTC CTCTCCCTAG    420

TGTTTGGACT CGCCTTAAAA TAATTGGCAG CCAGTGTTTT GGTAYTGAAG CGCAGCACAA    480

GTCGCGATTC TTATCAAATA CTTGCGTCCA CAAGCCCTTT TTTAACTTTT GACCTCGGAT    540

CAGGTAGGAG ACCGCTGACT TAA                                            563
```